US007604807B2

(12) United States Patent
Vodyanoy et al.

(10) Patent No.: US 7,604,807 B2
(45) Date of Patent: Oct. 20, 2009

(54) USE OF PULLULAN TO ISOLATE AND PRESERVE BIOLOGICAL MATERIAL

(75) Inventors: Vitaly J. Vodyanoy, Auburn, AL (US); James M. Barbaree, Dadeville, AL (US); Bryan A. Chin, Auburn, AL (US); William Charles Neely, Auburn, AL (US); Suram T. Pathirana, Sunnyvale, CA (US); Timothy D. Braden, Auburn, AL (US)

(73) Assignee: Auburn University, Auburn, AL (US)

( * ) Notice: Subject to any disclaimer, the term of this patent is extended or adjusted under 35 U.S.C. 154(b) by 365 days.

(21) Appl. No.: 11/341,152

(22) Filed: Jan. 27, 2006

(65) Prior Publication Data

US 2006/0172332 A1 Aug. 3, 2006

Related U.S. Application Data

(63) Continuation-in-part of application No. 10/000,727, filed on Nov. 30, 2001, now Pat. No. 7,022,514.

(60) Provisional application No. 60/250,798, filed on Dec. 1, 2000, provisional application No. 60/250,799, filed on Dec. 1, 2000.

(51) Int. Cl.
*C12N 1/04* (2006.01)
*C12N 5/06* (2006.01)
*C12Q 1/68* (2006.01)
*A01N 63/02* (2006.01)

(52) U.S. Cl. ........................ 424/195.18; 435/4; 435/260

(58) Field of Classification Search ............ 424/195.18; 435/4, 260
See application file for complete search history.

(56) References Cited

U.S. PATENT DOCUMENTS

| | | | |
|---|---|---|---|
| 3,235,337 A | 2/1966 | Artis | |
| 3,252,762 A | 5/1966 | Adams, Jr. et al. | |
| 3,645,852 A | 2/1972 | Axen et al | |
| 4,021,368 A | 5/1977 | Nemec et al. | |
| 4,115,534 A | 9/1978 | Ithakissios | |
| 4,284,553 A | 8/1981 | Brown et al. | |
| 4,329,337 A | 5/1982 | Sexton | |
| 4,391,909 A * | 7/1983 | Lim ........................... 435/1.1 | |
| 4,416,813 A | 11/1983 | Ikeda | |
| 4,504,582 A | 3/1985 | Swann | |
| 4,588,584 A | 5/1986 | Lumsden et al. | |
| 4,610,962 A | 9/1986 | Takagi et al. | |
| 4,632,904 A | 12/1986 | Lee | |
| 4,659,664 A | 4/1987 | de Buda | |
| 4,673,566 A | 6/1987 | Goosen et al. | |
| 4,708,932 A | 11/1987 | Axen et al. | |
| 4,933,284 A | 6/1990 | Lapins et al. | |
| 4,959,305 A | 9/1990 | Woodrum | |
| 4,971,783 A | 11/1990 | Bolton et al. | |
| 4,975,224 A | 12/1990 | Pringle | |
| 5,034,428 A | 7/1991 | Hoffman et al. | |
| 5,096,481 A | 3/1992 | Sylvia et al. | |
| 5,116,747 A | 5/1992 | Moo-Young et al. | |
| 5,144,008 A | 9/1992 | Ikeda et al. | |
| 5,227,298 A | 7/1993 | Weber et al. | |
| 5,268,286 A | 12/1993 | Kobayashi et al. | |
| 5,318,382 A | 6/1994 | Cahill | |
| 5,426,042 A * | 6/1995 | Maeda et al. ................ | 435/178 |
| 5,427,925 A | 6/1995 | Gearing et al. | |
| 5,474,890 A | 12/1995 | Di Virgilio et al. | |
| 5,550,178 A | 8/1996 | Desai et al. | |
| 5,554,286 A | 9/1996 | Okamoto et al. | |
| 5,627,063 A | 5/1997 | Divies et al. | |
| 5,648,091 A | 7/1997 | Sarama et al. | |
| 5,707,443 A | 1/1998 | Brown et al. | |
| 5,714,340 A | 2/1998 | Sutton et al. | |
| 5,728,350 A | 3/1998 | Kinoshita et al. | |
| 5,770,370 A | 6/1998 | Kumar | |
| 5,795,570 A | 8/1998 | Weber et al. | |

(Continued)

FOREIGN PATENT DOCUMENTS

| | | |
|---|---|---|
| DE | 3733551 A1 | 4/1989 |
| DE | 3733551 C2 | 4/1989 |
| EP | 0 699 905 | 3/1996 |
| FR | 2 732 240 | 3/1995 |
| GB | 865239 | 4/1961 |
| GB | 2 093 040 | 8/1982 |
| WO | WO 00/51573 | 9/2000 |

OTHER PUBLICATIONS

Yokohama, et al. "Deep Freezing of Horse Erythrocytes Cryo-protective Agents and Properties of the Cells Frozen Stored for 4 Years," Japanese Journal of Zootechnical Science; 1981; Abstract; pp. 487-492, vol. 52, No. 7.
Munderloh, et al., "Isolation of the Equine Granulocytic Ehrlichiosis Agent, *Ehrlichia equi*, in Tick Cell Culture," Journal of Clinical Microbiology; 1996; Abstract; pp. 664-670, vol. 34, No. 3.
Hayashibara. "Pullulan," Sep. 1, 2004. Online. Internet. Hayashibara International. Jan. 10, 2006 http://www.hayashibara-intl.com/food/pullulan.html.

(Continued)

*Primary Examiner*—Jon P Weber
*Assistant Examiner*—Kailash C Srivastava
(74) *Attorney, Agent, or Firm*—Andrus, Sceales, Starke & Sawall, LLP

(57) ABSTRACT

Compositions and methods for the reversible preservation of biological samples are provided. The compositions include natural polymers such as pullulan or acacia gum, including derivations and modifications thereof, which are usefull as a reversible preservation solution. A method is provided for using pullulan or Acacia Gum to isolate and reversibly preserve a biological specimen in a dormant state at room temperature for an extended period with minimal damage to the specimen. The compositions and methods disclosed may also be used to create reversibly preserved biological specimens and biological receptors for use in biosensors.

14 Claims, 24 Drawing Sheets

U.S. PATENT DOCUMENTS

| | | | |
|---|---|---|---|
| 5,827,707 | A | 10/1998 | Lamberti |
| 5,849,274 | A | 12/1998 | Gers-Barlag et al. |
| 5,866,356 | A | 2/1999 | Albert et al. |
| 5,916,029 | A | 6/1999 | Smith et al. |
| 6,043,067 | A | 3/2000 | Lihme et al. |
| 6,130,034 | A | 10/2000 | Aitken |
| 6,140,121 | A | 10/2000 | Ellington et al. |
| 6,309,815 | B1 | 10/2001 | Tash et al. |
| 6,391,296 | B1 | 5/2002 | Okano et al. |
| 6,413,713 | B1 | 7/2002 | Serebrennikov |
| 6,420,171 | B1 | 7/2002 | Nakamura |
| 6,472,160 | B2 | 10/2002 | Saruta et al. |
| 6,593,309 | B2 | 7/2003 | Ellington et al. |
| 6,596,310 | B1 | 7/2003 | Chou et al. |
| 7,022,514 | B2 | 4/2006 | Vodyanoy et al. |
| 2003/0091971 | A1 | 5/2003 | Xia et al. |
| 2003/0100103 | A1 | 5/2003 | Saruta et al. |
| 2003/0104506 | A1 | 6/2003 | Durst et al. |

OTHER PUBLICATIONS

Tilak R. Bhardwaj, et al. "Natural Gums and Modified Natural Gums as Sustained-Release Carriers" Drug Development and Industrial Pharmacy, 26(10), 2000: pp. 1025-1038.

D.J. Burgess et al., "Spontaneous Formation of Small Sized Albumin/acacia Coacervate Particles," J. Pharm. Phermacol. (1993) 45:586-591.

S.K. Baveja et al. "Examination of Natural Gums and Mucilages as Sustaining Materials in Tablet Dosage Forms," Indian J. Pharm Sci., (1988) 50(2): pp. 89-92.

D. Verbeken et al. "Exudate Gums: Occurrence, Production, and Applications" Appl. Microbiol Biotechnol (2003) 63:10-21.

Maria de Carmen de la Rosa et al. "Microbiological Quality of Pharmaceutical Raw Materials," Pharmaceutica Acta Helvetiae 70 (1995) 227-232.

Hiroaki Jizomoto et al. "Gelatin-Acacia Microcapsules for Trapping Micro Oil Droplets Containing Lipophilic Drugs and Ready Disintegration in the Gastrointestinal Tract," vol. 10, No. 8, 1993.

Biosensor—Wikipedia, the free encyclopedia, available on-line at http://en.wikipedia.org/wiki/Biosensor, at least as of Oct. 24, 2007.

Cranfield Biotechnology Centre—Biosensors: Past, Present and Future, available on-line at http://wwwlegacy.cranfield.ac.uk/biotech/chinap.htm, at lest as of Oct. 25, 2007.

International Search Report and Written Opinion; mailed Nov. 24, 2004; regarding International Application No. PCT/US2004/017872, "Use of Gum Acacia to Contain and Preserve a Biohazard" (European Patent Office).

International Search Report and Written Opinion; mailed Nov. 25, 2004; regarding International Application No. PCT/US2004/017873, "Use of Gum Acacia to Contain a Radiological Hazard" (European Patent Office).

Mallick H. et al; An experimental investigation of electrical conductivities in biopolymers; Bull. Mater. Sci., Aug. 2000; pp. 319-324; vol. 23, No. 4.

Tescione, L. and Gregor, A.; An Introductory Tutorial on Biosensor Technology; Dec. 1990 and Dec. 10, 1991.

* cited by examiner

USE OF PULLULAN TO ISOLATE AND PRESERVE BIOLOGICAL MATERIAL

CROSS REFERENCE TO RELATED APPLICATION(S)

This application is a Continuation-In-Part of U.S. patent application Ser. No. 10/000,727, filed Nov. 30, 2001, entitled "Use of *Acacia* gum to Isolate and Preserve Biological Material," now issued as U.S. Pat. No. 7,022,514, and further claims the benefit and priority of U.S. Provisional Application having Ser. No. 60/250,798, filed on Dec. 1, 2000, entitled "Method of Protection of Biosensor Surface," and U.S. Provisional Application having Ser. No. 60/250,799, also filed on Dec. 1, 2000, entitled "Method for Protection of Biological Material," all three of which are incorporated herein by reference.

TECHNICAL FIELD

The present invention relates generally to the field of biological sample preservation and, more particularly, to a method of using a solution of a protective natural polymer such as pullulan or *Acacia* gum to preserve a biological specimen in a dormant state and, later, using an aqueous solution to restore the specimen unharmed to its isolated condition.

BACKGROUND OF THE INVENTION

Various methods for the preservation of biological specimens have evolved over the years. Modem specimen preparation techniques for microbiology and electron microscopy typically include dehydration and immobilization, both of which are irreversible and often damage the integrity of the specimen.

Dehydration using chemicals or freezing temperatures typically causes structural damage to biological tissues. Chemicals may destroy the overall quality of the specimen, including the particular characteristics of interest to the scientist. Rapid freeze-drying often produces crystalline structures that are destructive to most biological tissues. The result of dehydration is a biological sample that has been significantly altered, beyond repair, from its natural state.

Immobilization of a biological sample within a polymer typically involves curing, using elevated temperatures or ultraviolet radiation, both of which are detrimental to specimen quality. The polymers and resins typically used for sample preparation today form a hard plastic when cured. Once a sample has been cured, the biological material cannot be restored to its isolated state.

Biological specimen preservation techniques are of particular concern in the preparation of biosensors. Biosensors are used in the health and environmental sciences for rapid detection of specific substances. Biosensors are currently used to detect the presence of pesticides, herbicides, and other compounds; to detect the presence of is organic compounds such as alcohols, ammonia, and metals; and, to detect the presence of specific bacteria including algae, fungi, and pathogenic organisms such as *Escherichia coli* (*E. coli*) and *Salmonella*. Potential applications for biosensors include sensing pollution and microbial contamination of air and water, clinical diagnosis of medical conditions, fermentation analysis and control, monitoring and analysis of industrial gases and liquids, monitoring of mining conditions and sensing toxic gases.

Biosensors often have a very short shelf life because the antibody or other biological receptor degrades rapidly when exposed to the environment. Like other biological samples, biological receptors need isolation and protection from the environment until ready for use. In field applications, especially, a variety of biological receptors may be needed at any time, depending upon the conditions.

There is an unsatisfied need in the art for biological samples that can be protected and preserved without altering or destroying the biological tissue. The demand for safe transport and prolonged storage of biological samples today requires preservation techniques that maintain the integrity and quality of the biological sample. Sensitive biological receptors used in biosensors need to be isolated from the environment, without damaging the receptor, until ready for use. None of the specimen preparation techniques in the art currently meet these needs.

There is also a need in the art for biological samples that can be restored to their isolated or prepared state after immobilization, with minimal damage, for later study or use. The current techniques of dehydration and immobilization are irreversible and destroy sample viability. Restoration is particularly critical for the biological receptors in biosensors, which are especially sensitive. There is a need, therefore, for a preservation technique that is both harmless and reversible.

SUMMARY OF THE INVENTION

The above and other needs are met by the present invention which, stated generally, provides a method of using a protective natural polymer such as pullulan or *Acacia* gum to isolate and preserve biological material without damage to the specimen. The present invention further provides reversible techniques for using a protective natural polymer such as pullulan or *Acacia* gum that maintain the integrity and viability of biological specimens, even after prolonged storage at room temperature.

In one aspect of the invention, a reversibly preserved biological specimen is provided. The specimen in an isolated condition has been combined with an effective amount of a solution of a protective natural polymer such as solid pullulan or solid *Acacia* gum dissolved in water. The suspension has been cured in ambient conditions to form a solid that can later be restored to a suspension. In one aspect, the suspension is capable of being separated so that the biological specimen can be restored to its former, isolated condition. In one embodiment, the biological specimen may include a separate container holding an effective amount of aqueous solution to restore the suspension by irrigating the solid in ambient conditions with the aqueous solution. The aqueous solution used to irrigate the solid may include distilled water, a buffer of 3-(N-morpholino) propanesulfonic acid, and one or more salts such as potassium chloride, sodium chloride, magnesium chloride, and/or calcium chloride.

In another aspect of the invention, a method of reversibly preserving a biological specimen includes the steps of combining the specimen in an isolated condition with an effective amount of a pullulan solution or an *Acacia* gum solution to form a suspension and, then, curing the suspension in ambient conditions to form a solid. The preservation method may also include the steps of irrigating the solid in ambient conditions with an effective amount of an aqueous solution to restore the suspension and then separating the solution from the specimen to restore the specimen to its former, isolated condition.

In one embodiment, the pullulan solution or the *Acacia* gum solution is formed by dissolving solid pullulan or solid *Acacia* gum in distilled water. The combining step may include immersing the specimen in the pullulan solution or the *Acacia* gum solution. The curing step may include stirring the suspension.

In one embodiment, the aqueous solution used to irrigate is the solid may include distilled water, a buffer, and one or more salts such as potassium chloride, sodium chloride, magnesium chloride, and/or calcium chloride. The buffer may be 3-(N-morpholino) propanesulfonic acid.

The biological specimens suitable for preservation may be microorganisms, viruses, bacteria, phages, antibodies, antigens, DNA, RNA, receptors, enzymes, proteins, biochemicals, yeast, fungi, plant and animal cells and extracts, semen, sperm, ova, blood, tissue samples, cell samples, urine, saliva, lymphatic fluid, skin, hair, bones, or bone marrow. In one embodiment, the biological specimen may be a biosensor.

In another aspect of the invention, a method of fabricating a reversibly preserved biological specimen includes the steps of combining the biological specimen in an isolated condition with an effective amount of a pullulan solution or an *Acacia* gum solution to form a suspension and, then, curing the suspension in ambient conditions to form a solid that can later be restored to a suspension. In one aspect, the suspension is capable of being separated so that the biological specimen can be restored to its former, isolated condition.

In one embodiment, the pullulan solution or the *Acacia* gum solution used in this method of fabrication is formed by dissolving solid pullulan or solid *Acacia* gum in distilled water. The curing step may include stirring the suspension. The combining step may include immersing the specimen.

In one embodiment, the method may include providing an effective amount of aqueous solution to restore the suspension by irrigating the solid in ambient conditions with the aqueous solution. The aqueous solution used to irrigate the solid may include distilled water, a buffer of 3-(N-morpholino) propanesulfonic acid, and one or more salts such as potassium chloride, sodium chloride, magnesium chloride, and/or calcium chloride.

In another aspect of the invention, a method of restoring the biological receptor includes the steps of irrigating the solid in ambient conditions with an effective amount of an aqueous solution to restore the suspension and, then, separating the solution from the biological receptor such that the biological receptor is substantially restored to its former, prepared condition. In one embodiment, the aqueous solution used to irrigate the solid may include distilled water, a buffer, and one or more salts such as potassium chloride, sodium chloride, magnesium chloride, and/or calcium chloride. The buffer may be 3-(N-morpholino) propanesulfonic acid.

In another aspect of the invention, a biosensor having a reversibly preserved biological receptor includes a signal transducer, an interface connected to the signal transducer, and a solid containing the biological receptor. The solid has been formed by curing a suspension in ambient conditions. The suspension includes the biological receptor in its prepared condition and an effective amount of a pullulan solution or an *Acacia* gum solution. The suspension is capable of being separated so that the biological receptor can be restored to its former, prepared condition.

In one embodiment, the pullulan solution or the *Acacia* gum solution is formed by dissolving solid pullulan or solid *Acacia* gum in distilled water. The biological receptors suitable for preservation may be microorganisms, viruses, bacteria, phages, antibodies, antigens, DNA, RNA, receptors, enzymes, proteins, biochemicals, yeast, fungi, plant and animal cells and extracts, semen, sperm, ova, blood, tissue samples, cell samples, urine, saliva, lymphatic fluid, skin, hair, bones, or bone marrow.

In one embodiment, the biosensor may include a separate container holding an effective amount of aqueous solution to restore the suspension by irrigating the solid in ambient conditions with the aqueous solution. The aqueous solution used to irrigate the solid may include distilled water, a buffer of 3-(N-morpholino) propanesulfonic acid, and one or more salts such as potassium chloride, sodium chloride, magnesium chloride, and/or calcium chloride.

In another aspect of the present invention, a method of reversibly preserving a biological receptor includes the steps of combining the receptor in its prepared condition with an effective amount of a pullulan solution or an *Acacia* gum solution to form a suspension and, then, is curing the suspension in ambient conditions to form a solid. The preservation method may also include the steps of irrigating the solid in ambient conditions with an effective amount of an aqueous solution to restore the suspension and then separating the solution from the receptor to restore the receptor to its former, prepared condition.

In one embodiment, the pullulan solution or the *Acacia* gum solution is formed by dissolving solid pullulan or solid *Acacia* gum in distilled water. The curing step may include stirring the suspension.

In one embodiment, the aqueous solution used to irrigate the solid may include distilled water, a buffer, and one or more salts such as potassium chloride, sodium chloride, magnesium chloride, and/or calcium chloride. The buffer may be 3-(N-morpholino) propanesulfonic acid.

In another aspect of the invention, a method of fabricating a reversibly preserved biological receptor disposed upon the interface of a biosensor includes the steps of combining the biological receptor in its prepared condition with an effective amount of a pullulan solution or an *Acacia* gum solution to form a suspension and, then, curing the suspension in ambient conditions to form a solid that can later be restored to a suspension. In one aspect, the suspension is capable of being separated so that the biological receptor can be restored to its former, prepared condition.

In one embodiment, the pullulan solution or the *Acacia* gum solution used in this method of fabrication is formed by dissolving solid pullulan or solid *Acacia* gum in distilled water. The curing step may include stirring the suspension. The combining step may include immersing the receptor.

In one embodiment, the method may include providing an effective amount of aqueous solution to restore the suspension by irrigating the solid in ambient conditions with the aqueous solution. The aqueous solution used to irrigate the solid may include distilled water, a buffer of 3-(N-morpholino) propanesulfonic acid, and one or more salts such as potassium chloride, sodium chloride, magnesium chloride, and/or calcium chloride.

In another aspect of the invention, a method of restoring the biological receptor includes the steps of irrigating the solid in ambient conditions with an effective amount of an aqueous solution to restore the suspension and, then, separating the solution from the biological receptor such that the biological receptor is substantially restored to its former, prepared condition. In one embodiment, the aqueous solution used to irrigate the solid may include distilled water, a buffer, and one or more salts such as potassium chloride, sodium chloride, magnesium chloride, and/or calcium chloride. The buffer may be 3-(N-morpholino) propanesulfonic acid.

In another aspect of the invention, a water-soluble solid for reversibly preserving a biological specimen includes a suspension formed by combining the biological specimen in an isolated condition and an effective amount of a solution of solid pullulan or solid *Acacia* gum dissolved in water and an effective amount of aqueous solution to restore the suspension by irrigating the solid in ambient conditions with the aqueous solution.

In one embodiment, the aqueous solution used to irrigate the solid may include distilled water, a buffer, and one or more salts such as potassium chloride, sodium chloride, magnesium chloride, and/or calcium chloride. The buffer may be 3-(N-morpholino) propanesulfonic acid.

The present invention thus provides an alternative method for preserving biological materials utilizing natural polymers such as pullulan or *Acacia* gum. Particular interest was in natural polymers because of their low cost and versatile applications. The present method has potential for protecting many different kinds of biological material, but especially genera of bacteria and forms of DNA, from adverse environmental conditions for an extended period of time without refrigeration. The preservation technique involves a single compound and simple procedure.

The simple design for preservation involves using a natural, non-toxic, biodegradable, water soluble polymer such as *Acacia* gum or pullulan to protect and preserve biological material such as microorganisms and DNA during desiccation and storage without refrigeration. The preservation process is inexpensive and does not incorporate sub-zero or elevated temperatures to cure bacteria in the polymer. This process is capable of preserving and transporting industrial size quantities of various biologicals for numerous applications. Such large-scale applications may include preserving bacteria for the food and agriculture industry, medicinal purposes, and crop protection. Preservation using natural polymers such as *Acacia* gum or pullulan could also be utilized to protect biologicals at crime scenes upon collection of samples in the field.

The present method of preserving biologicals using immobilization in protective natural polymers does not include any additives, accelerators, or plastifiers, nor does it involve elevated temperatures or radiation to promote polymerization. The polymerization and replacement of water occur spontaneously in a single process. The developed method is reversible, and the solid polymer can be safely removed from the biological material to recover viable cells or intact DNA throughout the duration of long-term storage at nonfreezing temperatures.

Further advantages of the present invention include: (1) compatibility with many biological materials, including structural, enzymatic, and immunological proteins, various DNA's, and microorganisms, (2) long-term preservation, and (3) recovery of the preserved materials via solubilization in water. The process is a simple, rapid, one step procedure. Hardening of the polymers is performed under simple conditions (no temperature above 40° C., no chemicals or radiation). The polymers are non-toxic and environmentally friendly, mechanically sound, and economically sound. The polymers can be used in any number of desirable forms and shapes including liquids, films, tablets, granules, and powder.

Thus, it is an object of the present invention to provide compositions and methods for protecting and preserving biological samples without altering or destroying the biological tissue. It is a related object to provide preservation techniques that maintain the integrity and quality of the biological sample.

It is a further object of the present invention to provide biological samples that can be restored to their isolated or prepared state after immobilization, with minimal damage, for later study or use. It is a related object of the present invention to provide a preservation technique that is both harmless and reversible.

It is a further object of the present invention to provide methods for restoring biological specimens and receptors to their former conditions without a significant loss in viability or function.

It is another object of the present invention to provide biosensors with biological receptors that can be restored to their prepared state after immobilization, with minimal damage, for later study or use.

It is yet another object of the present invention to provide a water-soluble solid for preserving biological specimens such that the specimens can later be restored to their isolated state with minimal damage.

These and other objects are accomplished by the method disclosed and will become apparent from the following detailed description of one preferred embodiment in conjunction with the accompanying drawings.

BRIEF DESCRIPTION OF THE DRAWINGS

In the drawings:

As shown in FIG. 3, a biosensor is comprised of a biological receptor, an interface, and a signal transducer. In FIG. 3, the biological receptor is deposited in a film 1 onto a piezoelectric crystal 2, which serves as the interface. An electrode 3 attached to the crystal acts as the signal transducer.

(FIG. 7A), 15° C. (FIG. 7B), 25° C. (FIG. 7C) and 40° C. (FIG. 7D).

(FIG. 11A), 15° C. (FIG. 11B), 25° C. (FIG. 11C) and 40° C. (FIG. 11D).

(FIG. 13A), 15° C. (FIG. 13B), 25° C. (FIG. 13C) and 40° C. (FIG. 13D).

(FIG. 13A), 15° C. (FIG. 13B), 25° C. (FIG. 13C) and 40° C. (FIG. 13D).

DETAILED DESCRIPTION OF THE INVENTION

The present invention, generally described, provides compositions and methods using protective natural polymers for the preservation of biological samples. The natural polymers are preferably *Acacia* gum or pullulan.

In one form, the compositions comprise *Acacia* gum, including derivations and modifications thereof which are useful as a reversible preservation solution. *Acacia* gum is a complex and highly branched carbohydrate polymer. The central core or nucleus is D- galactose and D-glucuronic acid, to which are attached sugars such as L-arabinose, L-rhamnose, and the like. *Acacia* gum is available as thin flakes, powder, granules, or angular fragments which are completely soluble in hot and cold water.

*Acacia* gum is a natural exudate or sap obtained from any of several plants belonging to the genus *Acacia*. *Acacia* Senegal and *Acacia* Seyal trees are the most commercially exploited species. *Acacia* gum typically refers to the gum harvested from *Acacia* Senegal trees.

*Acacia* plants are leguminous shrubs and trees that grow in warm regions, such as the Republic of the Sudan and the Upper Nile region of eastern Africa, where most of the world's *Acacia* gum is harvested.

*Acacia* gum was widely used in ancient Egypt in the preparation of inks and dyes and is thought to have been used as an adhesive for mummification bindings. An article of commerce for centuries, the name "Arabic Gum" is believed to have been derived from the fact that *Acacia* gum was typically shipped from Arabian ports to Europe. Today, *Acacia* gum is used in the manufacture of printing inks, textile dyes, adhesives, pharmaceuticals, vitamins, confections, foods, beverages, cosmetics, and many other products. For example, *Acacia* gum is used to make the water-soluble glue on postage stamps and envelopes, added to candies to prevent crystallization, used as a coating to flavor particles and beverages, added to beer to stabilize the foam, used as an emulsifier of fats in foods, lotions, and soaps, and is the most important gum in the manufacture of ink.

The botanical name for the *Acacia* gum referred to in this application is *Acacia* Nilotica (Linn), N. O. Leguminosae. *Acacia* gum is water-soluble, edible, non-toxic, highly uniform, pale in color, and has excellent emulsifying and film-forming qualities. *Acacia* gum consists mainly of high-molecular weight polysaccharides and their calcium, magnesium and potassium salts.

Figure 1:
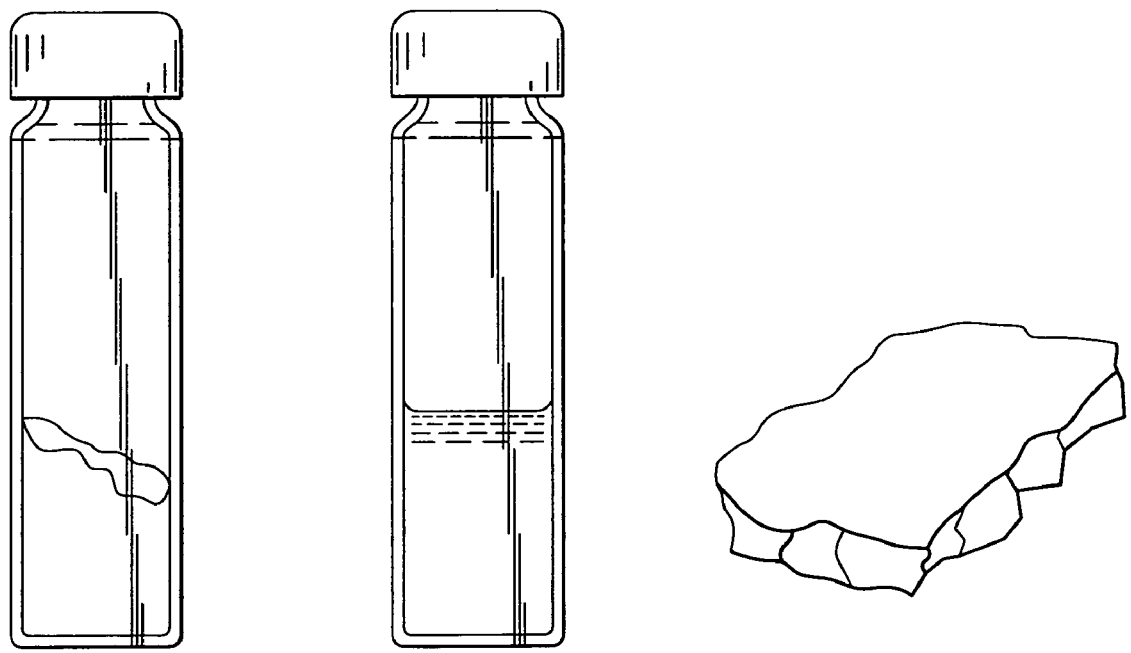
FIG. 1 includes line drawings showing *Acacia* gum powder in the vial on the left, *Acacia* gum in aqueous solution in the other vial, and a solid sheet of *Acacia* gum at room temperature.
Figure 2A:
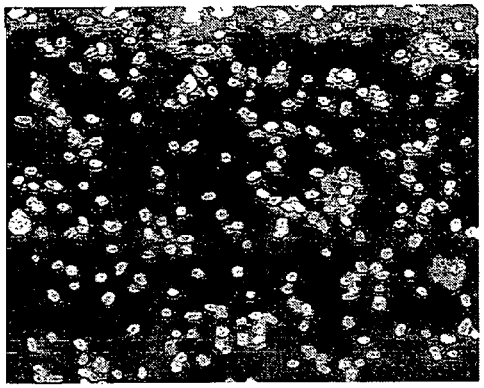
FIG. 2 shows a series of photographs of *Salmonella* bacteria at various stages of immobilization and restoration, according to an embodiment of the present invention. Slide 2A shows the bacteria immersed in the *Acacia* gum solution. Slide 2B shows the bacteria immobilized within the *Acacia* gum solution, which has become a solid at room temperature. The restoration process is shown in Slides 2C (one minute), 2D (two minutes) 2E (three minutes), and 2F (ten minutes).
Figure 2B:
Figure 2C:
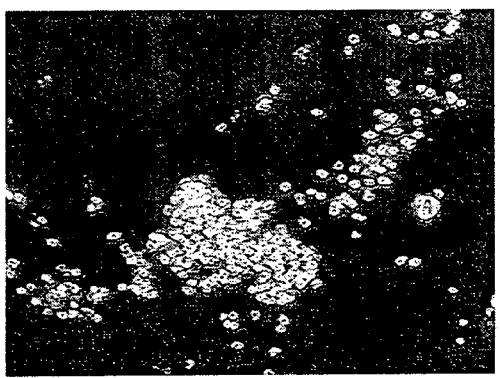
Figure 2D:
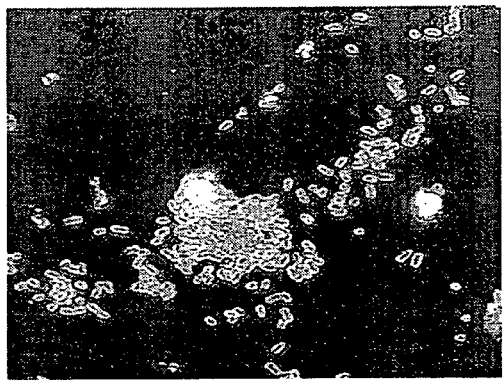
Figure 2E:
Figure 2F:
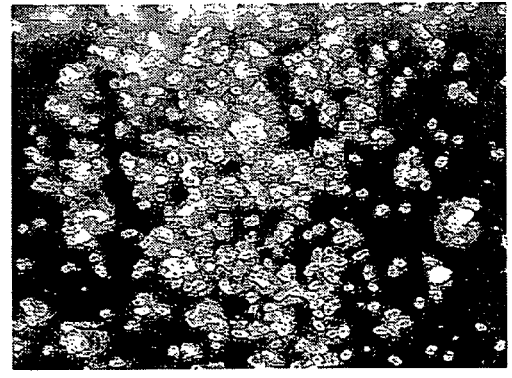

*Acacia* gum is harvested by tapping the trunk of an *Acacia* Senegal tree, which causes the gum to seep out and solidify into colorless or pale yellow tear-shaped nodules. The dried nodules are typically gathered by hand. *Acacia* gum is commercially available in the form of white or yellowish flakes, granules, or powder. *Acacia* gum powder is plentiful and readily available commercially, at a low cost. When the powder form is dissolved in water, the resulting solution becomes increasingly viscous as the water evaporates, becoming a solid at room temperature. The photograph in FIG. 1 shows *Acacia* gum powder in the vial on the left, *Acacia* gum in aqueous solution in the other vial, and between the vials a solid sheet of *Acacia* gum at room temperature.

In a second form, the compositions comprise pullulan, including derivations and modifications thereof, which are useful as a reversible preservation solution. Pullulan is a natural, linear homo-polysaccharide polymer consisting of maltotriose units linked through $\alpha$-1,6-glycosidic bonds. Pullulan is also known as $\alpha$-1,4-; $\alpha$-1,6-glucan. Pullulan is produced from starch via fermentation by the fungus Aureobasidium pullulans. Pullulan is available as a white powder, and is odorless, flavorless, edible, biodegradable, water-soluble, non-toxic, non-mutagenic and highly stable. This polymer forms solutions of low viscosity, and has numerous uses in foods, pharmaceuticals, manufacturing, and electronics similar to that of *Acacia* gum.

The compositions of the invention are useful for the preservation of any biological sample of interest. Such samples include, without limitation, microorganisms, viruses, bacteria (such as *E. coli, Salmonella, Listeria, Staphylococcus, Bacillus subtilis*, and others), phages, antibodies, antigens, DNA (e.g. ssDNA and dsNDA), RNA, receptors, enzymes, proteins, biochemicals, yeast and other fungi, and plant and animal cells and extracts. Animal cells and samples, urine, saliva, lymphatic fluid, skin, hair, bones, and bone marrow. Additionally, biological samples include proteins, enzymes, antibodies, monoclonal antibodies and the like.

The phrase, "biological specimen in an isolated condition," as used herein indicates a biological sample that has been isolated and substantially purified; meaning that it is substantially or essentially free from components that normally accompany or interact with the sample as found in its natural environment.

Isolation and Preservation Technique

*Acacia* gum powder and pullulan powder are both readily soluble in water. The solution becomes increasingly viscous as some of the water evaporates. An aqueous pullulan solution as well as an aqueous *Acacia* gum solution is characterized by its reversibility. If more water is added, the viscosity decreases. Even if the solution is permitted to harden or cure into a solid, the addition of water will return the solid to an aqueous solution. Reversibility in this context also refers to the fact that both the pullulan solution and the *Acacia* gum solution can be separated nearly completely from the biological specimen after the preservation method of the present invention has been performed.

In one embodiment of the present invention, a biological specimen is preserved by being immersed in or otherwise combined with an effective amount of pullulan, a pullulan solution, *Acacia* gum, an *Acacia* gum solution, or a mixed *Acacia* gum and pullulan solution. The amount of pullulan solution or *Acacia* gum solution will vary depending upon sample size. The phrase "effective amount" is intended to indicate an amount sufficient to form a suspension; that is, to suspend the biological molecules or units of the specimen within the pullulan solution or *Acacia* gum solution.

Initially upon being immersed in the solution, biological material such as bacteria remain active and motile. As the viscosity increases, activity and motility decrease. In one embodiment, the suspension may be stirred to ensure a good distribution of specimen or to speed the evaporation of water and thus accelerate the curing process. Curing may take place in ambient conditions; in other words, at room temperature and at normal atmospheric pressures. When the solution solidifies, the bacteria shrink to about one-half to one-third of their original size. While the invention is not bound by any particular mechanism of action, it is postulated that the pullulan solution and/or the *Acacia* gum solution penetrates the cell membrane of the biological material, possibly replacing the water and resulting in the overall shrinkage observed. Inside the resulting solid, the bacteria remain dormant and may be kept at room temperature.

In one embodiment, the solid material containing the biological specimen may be made into a powder, pellets, tablets, flakes, plates, capsules, or other forms or containers. The solid is transparent to visible light, a feature that makes it suitable for viewing and for certain optical applications. Moreover, although the solid is water-soluble, the solid is resistant to almost all organic solvents and most acids.

To restore the biological material to its isolated condition, the solid is irrigated with an aqueous solution. The amount of aqueous solution needed to change the solid back into a suspension will vary depending upon the sample size. The phrase "effective amount of aqueous solution" is intended to indicate an amount sufficient to transform the solid into a suspension.

In one aspect of the invention, the aqueous solution used to irrigate the solid contains distilled water, a buffer, and one or more salt compounds such as potassium chloride, sodium chloride, magnesium chloride, and calcium chloride. The buffer is a substance capable in solution of neutralizing both acids and bases and, thereby, maintaining the original pH of the solution. One such pH buffer in common use is 3-(N-morpholino) propanesulfonic acid (also known as MOPS). Another common pH buffer is called a phosphate buffer. A phosphate buffer, in one form, contains anhydrous monosodium phosphate and trisodium phosphate dodecahydrate. A phosphate buffer solution may contain different molar ratios of monosodium phosphate and trisodium phosphate, depending upon the value of the pH to be maintained.

When irrigated, the solid gradually dissolves and the biological specimen is again suspended within either the pullulan solution or the *Acacia* gum solution. The viscosity of the suspension decreases as more aqueous solution is added. The biological specimen returns to its normal size, absorbing the water lost or exchanged during the curing process.

In another aspect of the present invention, the suspension of biological material and polymer solution is reversible because it can be separated. The pullulan solution and/or the *Acacia* gum solution can be removed using common methods of separating mixtures, leaving the biological specimen in its isolated condition. The separation step restores the biological specimen to its former isolated or prepared condition. The phrase "substantially restored" is intended to describe the nearly complete separation of the polymer solution from the biological specimen and the nearly complete restoration of viability of the biological specimen.

Biosensors

Figure 3:
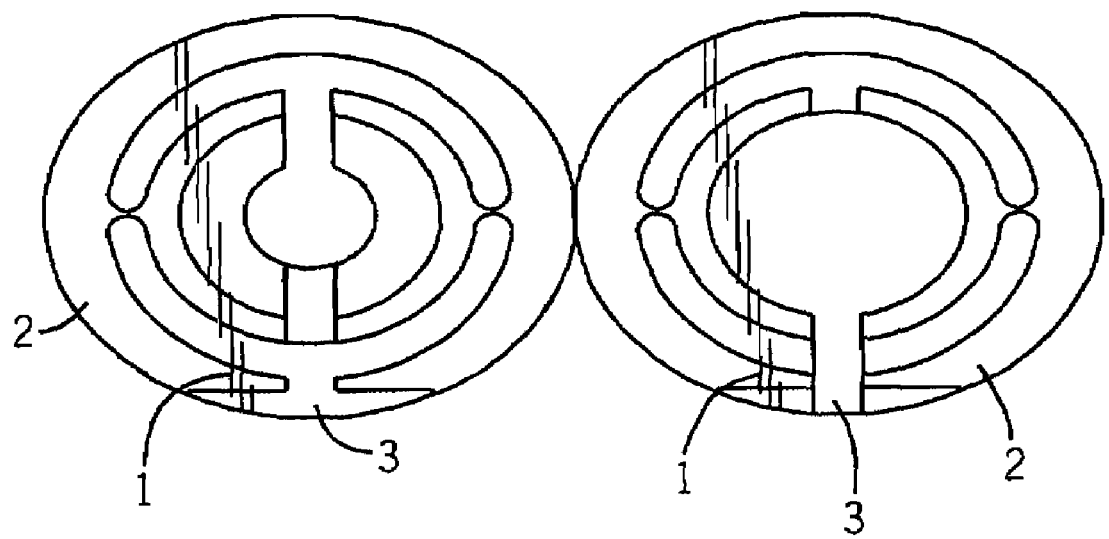
FIG. 3 includes line drawings of crystal biosensors coated with a film of *Acacia* gum solution, according to an embodiment of the present invention.

The methods of the invention find particular use in preserving biological samples on biosensors. A biosensor, as shown in FIG. 3, is comprised of a biological receptor, an interface, and a signal transducer. The biochemical signal produced when a sample is placed on the biological receptor is converted or translated by the signal transducer into a quantifiable electrical signal.

The biological receptor is selected to sense a specific target compound called the analyte. For example, a copper receptor will absorb copper molecules from a sample. The signal transducer converts the activity on the receptor (e.g., the accumulation of copper molecules) into an electrical signal. For example, the signal transducer can detect the increased mass of the biosensor by sensing changes in certain electrical properties.

The types of biological receptors in use include, without limitation, enzymes, antibodies, phages, and lipid layers. The biological receptor must be prepared such that it will respond to the analyte. Preparation of the biological receptor includes depositing the biological material onto the interface. Preparation of the interface to receive the biological receptor may include chemical etching of the interface, the application of thin membranes, coating the interface with a thin layer of a particular biochemical to serve as an anchor for the biological receptor, or any other of a variety of preparation methods. The phrase, "biological specimen in a prepared condition," as used herein indicates a biological receptor that has been isolated and deposited upon the biosensor interface using any preparation technique that renders the receptor ready for its intended use.

The signal transducer is typically an electrode connected to the interface to measure any change in the receptor when the sample is introduced. Signal transducer systems include, without limitation, piezoelectric crystals, conductimeters, enzyme-sensing electrodes, thermistors, optoelectronic and fiber-optic devices, field-effect transistors, gas-sensing electrodes, and ion-selective electrodes. The signal transducer itself may be a pH-electrode, an oxygen electrode, or a piezoelectric crystal.

In a common biosensor using quartz crystal technology, shown in FIG. 3, the biological receptor is deposited in a film 1 onto a piezoelectric crystal 2, which serves as the interface 3. An electrode attached to the crystal acts as the signal transducer. The quartz crystal is oscillated at a known frequency based on its total mass, including the mass of the film receptor. When a sample containing the analyte is placed on the receptor, the total mass will change when the antibodies in the receptor bind to the analyte. In response to the change in mass, the frequency of the crystal oscillation will change, and the change in frequency is measured by the signal transducer. Because frequency and mass are related, the additional mass can be calculated, indicating the precise amount of the analyte present in the sample.

The Biosensor Experiment

Figure 4:
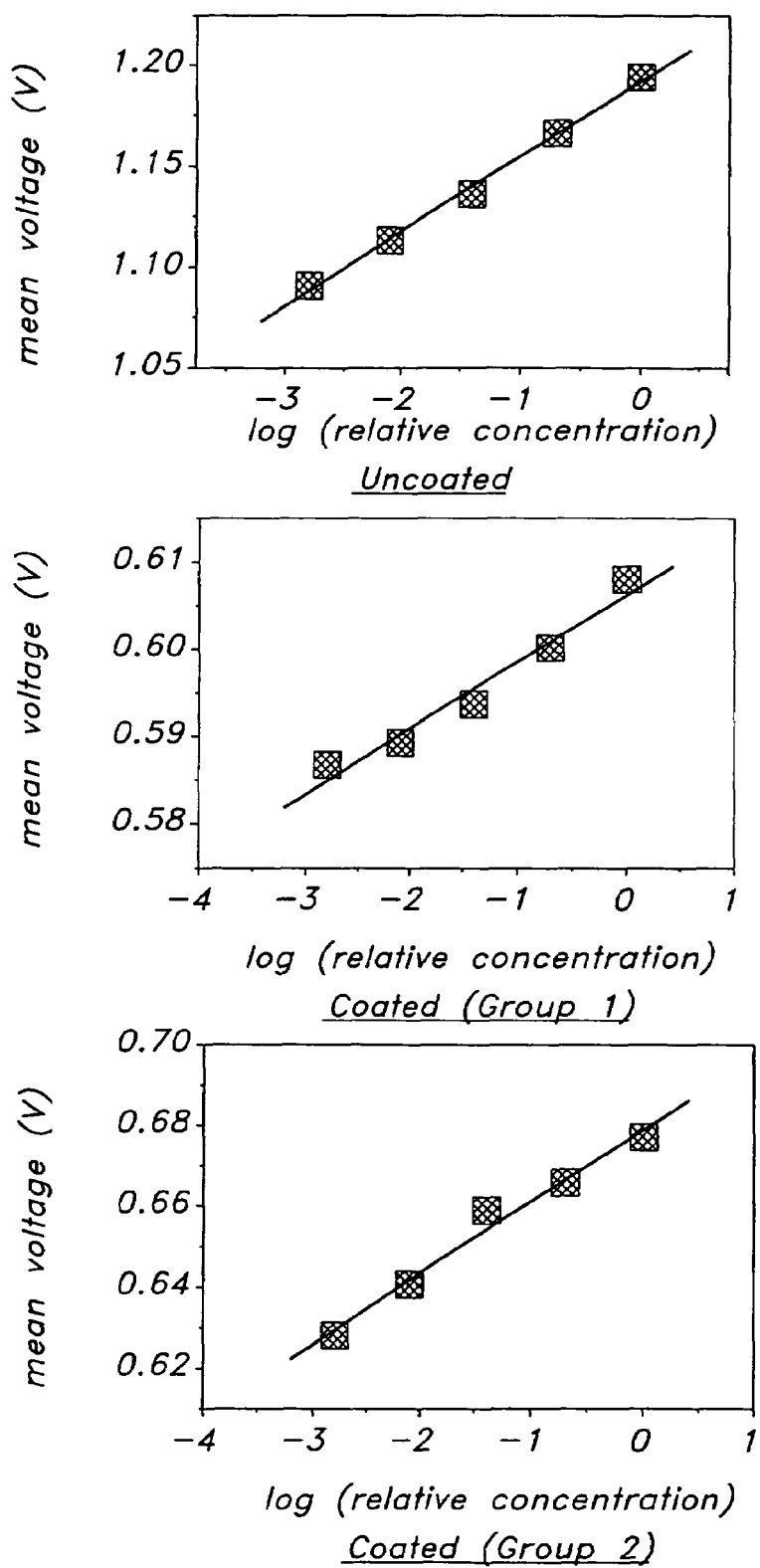
FIG. 4 is a series of graphs representing the results of experimentation conducted according to an embodiment of the present invention.

A biosensor with a biological receptor comprised of antibodies against *Salmonella* bacteria was covered with a film of *Acacia* gum solution. After curing and storage at room temperature for a period of four (4) days, the antibodies were released by irrigation with water containing 55.0 milli-Molar potassium chloride, 4.0 milli-Molar sodium chloride, 1.0 milli-Molar magnesium chloride, 0.1 milli-Molar calcium chloride, and 2.0 milli-Molar 3-(N-morpholino) propanesulfonic acid, used as a pH buffer. Preliminary data was obtained demonstrating the sensitivity of the restored sensors compared to the uncoated sensors, as shown in FIG. 4 and Table One.

TABLE ONE

Performance of Coated *Salmonella* Biosensors

| | Uncoated | Coated (Group 1) | Coated (Group 2) |
|---|---|---|---|
| Total Sensors | 9 | 4 | 22 |
| Good Sensors | 4 | 1 | 8 |
| Yield (%) | 44.4% | 25.0% | 36.4% |
| Slope (mV per decade) | 15.3 | 7.6 | 19.4 |

Measurements were carried out with a Quartz Crystal Microbalance (QCM) measurement system. More specifically, the biosensors used in this experiment were the PM-700 series quartz sensor crystals available from Maxtek, Inc. The output of the sensor crystal corresponds to the change in total mass. The signal transducer measures the change in the crystal in millivolts (mV). Referring to Table One and the graphs shown in FIG. 4, the "mV per decade" refers to the voltage change for each order of magnitude change in the bacterial concentration.

The bacterial suspension of approximately $10^9$ cells per milliliter was diluted 10, 100, and 1000 times, respectively. The relative concentrations of bacteria were, therefore, 1, $10^{-1}$, $10^{"2}$, and $10^{-3}$. Accordingly, the logarithms (shown in FIG. 4) of the relative concentrations were 0, −1, −2, and −3, respectively.

For purposes of this experiment, a "good sensor" has a sensitivity of more than 7.0 mV per decade. The observation that only 44.4 percent of the uncoated biosensors were "good sensors" indicates the inherent fragility of the biological receptors used in biosensors.

The slope of the graphs shown in FIG. 4 indicates the degree of sensitivity of the biosensor. The uncoated biosensors had a sensitivity of 15.3 mV per decade. While the sensitivity of Group 1 decreased to 7.6 mV, the sensitivity of the coated biosensors in Group 2 was observed to be 19.4 mV—better than the sensitivity of the uncoated sensors. In both cases, the biosensors which had been coated with the *Acacia* gum solution were fully operational and ready to use.

The Bull Sperm Experiment

In another aspect, the methods of the invention are useful in preserving animal cells and extracts, such as sperm. In another experiment, the isolation and preservation technique of the present invention was used to temporarily and reversible preserve bull sperm.

A sample of bull sperm was immobilized in *Acacia* gum solution, where it remained at room temperature for a period of four (4) days before being released by irrigation with water. Although reproduction was not tested, the bull sperm showed no difference in motility when compared to the initial sample.

The present invention may be used to preserve bull sperm for transport or storage, at room temperature, without significant damage to the sperm. The cryogenic preparation and storage of bull sperm is expensive and destructive because of crystalline structures formed during freezing. In contrast, the present invention does not introduce crystals or other destructive structures into the sample and it is much less expensive.

Bacterial Cultures

The methods of the present invention are also useful in preserving samples of bacteria. Two separate experiments were conducted to test the response and subsequent viability of bacteria suspended within an *Acacia* gum solution.

In a first experiment, separate samples of *Escherichia coli* 0157 (*E. coli*) bacteria and *Salmonella* bacteria were immobilized in *Acacia* gum solution, where each sample remained at room temperature for a period of seven (7) days. The bacteria were released by irrigation with water containing a phosphate buffer (pH 7.4) containing 2.7 milli-Molar potassium chloride and 137 milli-Molar sodium chloride. The released bacteria showed no difference in motility when compared to the initial culture. The bacteria reproduced normally.

FIGS. 2A-2B show the *Salmonella* bacteria at different stages of the experiment. FIG. 2A shows the bacteria immersed in the *Acacia* gum solution. FIG. 2B shows the bacteria immobilized within the *Acacia* gum solution, which has become a solid at room temperature. Notice that the bacteria in FIG. 2B are somewhat smaller.

After remaining immobilized for seven (7) days, the is bacteria were irrigated with an aqueous solution. The restoration process is shown in FIGS. 2C, 2D, 2E and 2F. FIG. 2C shows the condition of the bacteria after one minute. Some motion was observed after two minutes, shown in FIG. 2D. FIG. 2E shows the condition of the bacteria after three minutes. After ten minutes, as shown in FIG. 2F, the bacteria have returned to their normal size, absorbing the water lost during the immobilization or curing process.

In a second experiment, two additional samples of *E. coli* and *Salmonella* bacteria were immobilized in *Acacia* gum solution for a period of twenty-one (21) days, with the same results. The bacteria showed no difference in motility when compared to the initial culture and the bacteria reproduced normally.

Additional Experiments

In a third experiment, *Escherichia coli* (*E. coli*) preservation experiments are described. These experiments include optimizing *Acacia* gum concentration, determining optimal container for samples, and drying method. Additionally, experiments testing viability of *E. coli E. coli* after long-term storage under various temperatures and humidity are described.

In a fourth experiment, *Bacillus subtilis* spore (*B. subtilis*) preservation experiments are described. These experiments include optimizing *Acacia* gum concentration, determining optimal container for samples, and drying method. Additionally, experiments testing viability of *B. subtilis* spores after long-term storage under various temperatures and humidity are described.

In a fifth experiment, the optimal *Acacia* gum concentration and method of drying for preserving ssDNA and dsDNA are described. This experiment also includes results from long-term preservation of both types of DNA stored at various temperatures and humidity.

The biologicals used to study *Acacia* gum's and pullulan's capacity for protecting biologicals during desiccation and storage in experiments three and four include *E. coli* and *B. subtilis*, and in the fifth experiment include single-stranded deoxyribonucleic acid (ssDNA) and double-stranded DNA (dsDNA). The methods used to test the integrity of these biologicals before and after drying and during storage were tittering for bacteria, and gel electrophoresis and PCR for DNA.

Bacteria

The bacteria selected to represent gram-negative non-spore forming bacteria and gram-positive, spore forming bacteria was *Escherichia coli* ATCC 11775 and *Bacillus subtilis* ATCC 6051, respectively. These strains of bacteria are chosen because they are well characterized, non-pathogenic, economical and widely used.

Deoxyribonucleic Acid

There were two types of DNA used in experiment 5. ssDNA and dsDNA which were isolated from fd-tet bacteriophage. This phage is a filamentous virus that contains a single-stranded DNA genome. This type of phage infects K91 BKan *Escherichia coli* via attachment to bacterial pilus. Once phage ssDNA is inside of the bacterial cell, it replicates the viral genome via rolling circle method using bacterial enzymes. During this process, the ssDNA (phage genome) is complimentarily base paired and becomes double stranded. The phase dsDNA within a bacteria cell is the replicative form (RF) by which copies of the phage genome are produced in order for phage to proliferate. This type of RF DNA is covalently closed circular dsDNA. Thus, the ssDNA is isolated from phage itself, and the dsDNA is isolated from bacterial cells infected with phage.

Experiment 3

Introduction

Experiment 3 focuses on developing a simple process for preserving *E. coli* in protective polymers without using specialized equipment or complex formulations. This method involves bacteria suspensions mixed with AG polymer and air dried at 40° C. The samples were stored at various temperatures and humidity, and tested for viability before and after drying and during storage. AG polymer was compared with a physiological buffer (PBS) and a natural polysaccharide (pullulan) produced by a fungus, Aureobasidium pullulan. These solutions were mixed with bacterial suspensions in the same ratio as AG and dried at 40° C. Successful preservation of bacteria was indicated by viability testing via colony plate count method.

Materials and Methods

Materials

Acacia gum (AG) and pullulan polymer powders were purchased from Frontier™ Natural Products Co-Op (Norway, Iowa), and Sigma-Aldrich (St. Louis, Mo., cat # P-4516), respectively. Salts, listed in Table 1, were purchased from Fisher Scientific (Hampton, N.H.): potassium carbonate (cat # P179-500), ammonium chloride (cat # A687-500), potassium nitrate (cat # P263-500), calcium nitrate (cat # C109-500), and ammonium sulfate (cat# A938-500).

Polymer Preparation

Polymer solutions were prepared by mixing polymer powders with sterile water in content ations of 10, 15, 20 or 25% w/v and stirred for 2-3 h, or until powder was completely dissolved. AG colloidal solutions were filtered using two Brew Rite® coffee filters (Rockline Industries, Sheybogan, Wis.) in a Btichner funnel with vacuum filtration. Filters were changed after every 10-20 ml and the solutions were filtered twice and autoclaved at 120° C. for 15 min, cooled and stored at 4° C. The pullulan polymer solutions were sterilized by filtration using 0.22 μm Millipore Stericup™ (Fisher Scientific, cat # SCGV-U01-RE). The Stericups containing pullulan were capped, covered with aluminum foil, and stored at 4° C.

Long-Term Sample Storage Conditions

There were two types of long-term preservation experiments conducted for all biologicals: (1) storage at various temperatures and constant humidity and (2) storage at various humidity and constant temperature. Usually, samples were tested on days 2, 4, 8, 16, 32, 64, and 128 of experiments. For temperature experiments, samples were sealed after drying and placed in holding containers. Samples were stored in incubators set at 5, 15, 25, and 40° C. and constant humidity (~33%) for long-term storage.

TABLE 2.1

Saturated salt solutions at 25° C.
Saturated salt solutions were prepared and placed in RH chambers. To insure complete saturation, additional salt crystals were added to the saturated solutions in the RH chambers.

| Humidity, % | Salt | Salt, g | $H_2O$, ml |
|---|---|---|---|
| 46 | $K_2CO_3 \cdot 1.5H_2O$ | 200 | 100 |
| 53 | $Ca(NO3)2.6H20$ | 470 | 100 |
| 76 | $KNO_3 + NH_4Cl$ | 50 + 50 | 100 |
| 86 | $(NH_4)_2SO_4$ | 100 | 100 |

For humidity experiments, saturated salt solutions were used to maintain, 46, 53, 76, and 86% o relative humidity (RH) at 25° C. (Table 1). Each salt, if mixed to saturation point in water, maintains an associated characteristic RH at a given temperature in the microenvironment in the RH chambers. For example, if air of low relative humidity is introduced into the chamber, water molecules will evaporate from the saturated solution until the characteristic RH is achieved. Conversely, if air of high relative humidity is introduced, the solution will absorb water molecules from the air until that RH is reached. Samples were placed uncapped in RH chambers containing saturated salt solutions. RH chambers with samples were sealed and put in a large incubator set at 25° C. for long-term storage.

*E. Coli* Cultivation and Preparation of Concentrated Cell Suspension

*Escherichia coli* (ATCC 11775) was purchased from American Type Culture Collection in Manassas, Va. Fresh *E. coli* cultures were grown in Difco nutrient broth (Fisher cat # DF0003) for 18 h in a shaker incubator set at 200 rmp and 73° C. Bacterial cells were harvested by centrifuging for 10 min at 5,000 rpm; then the supernatent was discarded. The concentrated cell suspensions were prepared by adding 1 ml of PBS to each pellet formed from 50 ml of original culture.

Estimation of Viability of Bacterial Samples

Bacterial titers were determined before drying, after drying and after storage on days specific for type of experiment. For re-hydration of samples, sterile de-ionized water was added in the amount of water loss and incubated at ambient temperature for 30-45 min. Bacterial viability was estimated by preparing serial dilutions and plating 10 μl of each dilution on Difco nutrient agar obtained from Fisher Scientific (cat # DF0001-17-0). The bacteria were grown under aerobic conditions in a 37° C. incubator for 18-24 h. The dilutions that contained 30-300 colonies were counted. Data were expressed as colony forming units per ml (CFU $ml^{-1}$). The bacterial colonies were observed for any morphological or pigmentation changes.

Optimization Experiments

Short-term experiments were performed to determine the optimal conditions for long-term storage of *E. coli* samples. These conditions included AG concentration, drying temperatures, sample volume and container.

Polymer Concentration Determination Procedure

Small polystyrene Petri plates purchased from Fisher (cat #08772-30) were labeled. One part concentrated *E. coli* suspension was mixed with four parts of 10, 15, 20 or 25% AG. Five hundred microlites of these *E coli* suspensions in AG were aliquoted into these dishes. These samples were dried uncovered in 40° C. incubator (Lab Line Imperial III Model 302, Fisher, cat #11-702-10) containing silica desiccant beads for ~20 h. Dried samples were covered and stored at 25° C. Bacterial viability was estimated before and after drying and after storage for 2 and 6 days as described in section 2.2.3.

Container, Sample Volume and Drying Temperature Determination Procedure

*E. coli* bacterial suspensions in 15% AG and PBS were prepared as described in section 2.4.1 and aliquoted into containers as outlined in Table 2. The following containers used in optimization experiments were purchased from Fisher: 2.0 ml microcentrifuge tubes (cat #05-408-138), 6 well plates (cat #08-772-49), (3.5 cm) small Petri plates, and 12.5 cm$^2$ cell culture flasks (cat #08-772-1F). Table 2 summarizes the parameters of sample volume, drying temperature, type of drying and time to dry. Bacterial viability was estimated via the plate count method before and after drying.

Long-Term Storage Experiments for *E. Coli* Samples

Based on optimization procedures, the following protocol was used for long-term preservation of *E. coli* cells. Bacterial suspensions in 15% AG, 15% pullulan, and PBS were prepared as described in section 2.4.1. An aliquot of 500 µl of sample was placed into a labeled small Petri plates. The plates were placed in an incubator containing silica desiccant and were dried at 40° C. for 22-24 h.

For temperature experiments, dried samples were capped and placed into 470 ml square containers which were sealed with paraffin. These containers were stored at 5, 15, 25, and 40° C. Bacterial viability and stability were tested as described herein, before and after drying and after storage on days 2, 4, 8, 16, 32, 64, and 128. For humidity experiments, samples dried in small Petri plates were placed in redi-tip boxes, which were placed in 470 ml square Rubbermaid® container holding saturated salt solutions. The containers were sealed tightly with lids and reinforced with paraffin to prevent water evaporation during long-term storage. The RH chambers were sealed and stored at 25° C. Bacterial viability and stability were tested as described herein, before and after drying and after storage on days 2, 4, 8, 16, 32,-64, and 128.

TABLE 2.2

Summary of parameters for optimizing the drying method for bacteria in AG.

| Container | Sample Volume, µl | Drying Temp, °C. | Method of drying | Time to dry, hr |
|---|---|---|---|---|
| 2.0 ml microcentrifuge tubes | 50, 100 | Ambient | Vacuum centrifuge | 5 |
|  | 50, 100 | Ambient | High vacuum | .75 |
| 6 well plates | 500 | Ambient | Circulating air under laminar hood | 4 |
|  | 500 | 40 | Static air incubator | 5 |
|  | 500 | 37 | Static air incubator | 5 |
| Small Petri plates (3.5 cm) | 50 | Ambient | Vacuum desiccator | 3.5 |
|  | 50 | 40 | Static air incubator | 2 |
|  | 500 | Ambient | Vacuum desiccator | 6 |
|  | 500 | 40 | Static air incubator | 20 |
| Culture flasks (12.5 cm$^2$) | 500 | 25 | Static air incubator | 72 |
|  | 500 | 40 | Static air incubator | 48 |
| Glass vials (7.4 ml) | 500 | 40 | Static air incubator | 48 |

Results and Discussion

Optimization Experiments for Long-term Preservation of *E. Coli*

Numerous dehydration and short-term storage experiments were performed to optimize conditions for sample preservation and analysis; among them, determination of AG concentration, storage containers, drying temperature, method of drying and duration of drying, and storage temperature. In order to compare AG to a substance with similar applications, natural pullulan polymer was used as a control polymer.

Figure 5:
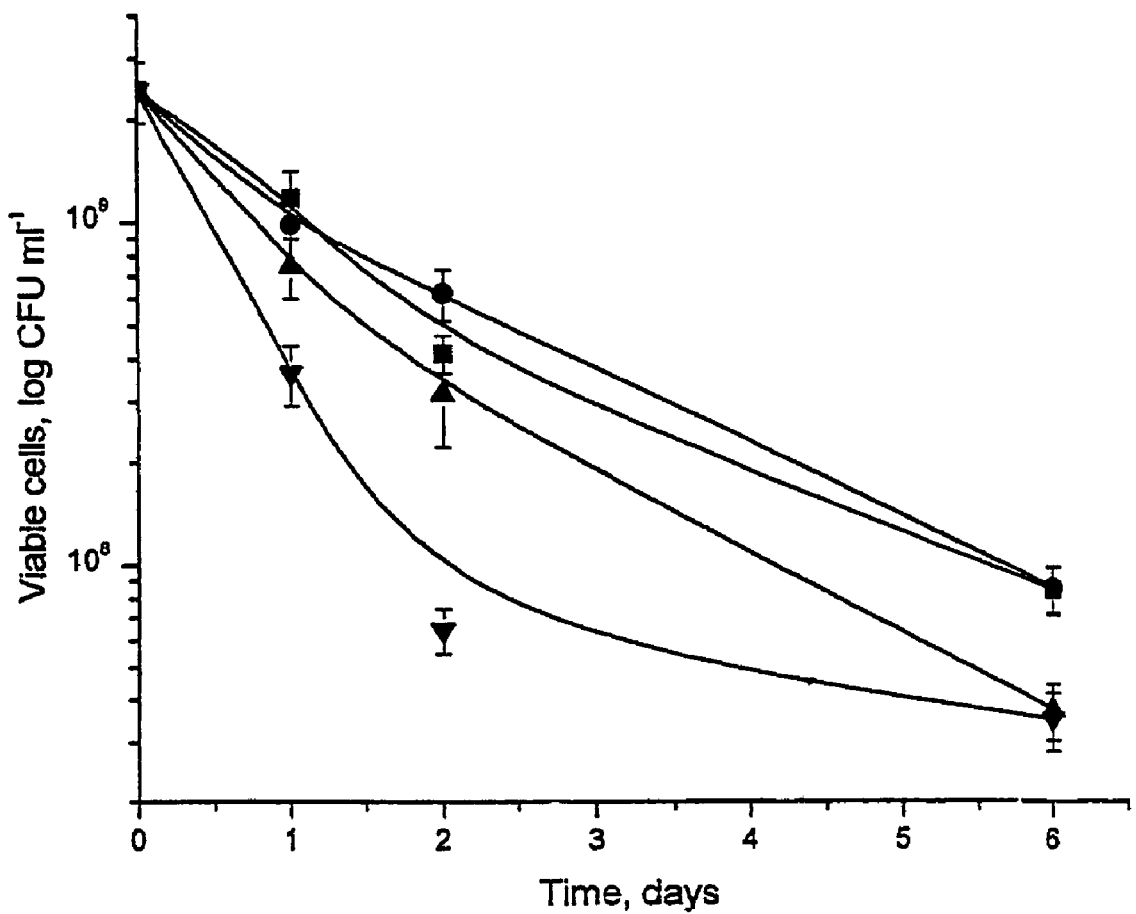
FIG. 5 is a graph illustrating viability of *E. coli* cells preserved at various AG concentrations in accordance with experiment 3 where AG was prepared in concentrations of 10% (■), 15% (●), 20% (▲), and 25% (▼).

To find the optimal AG concentration for preservation of *E coli*, the viability of bacteria was tested when dried and stored for six days in various polymer concentrations ranging from 10-25%. Degradation curves for *E coli* in all concentrations of AG shown in FIG. 5. The percent of viable cells remaining after drying of *E. coli* samples in 10, 15, 20 and 25% was 48.5, 40.4, 30.7 and 14.9%, respectively. More viable cells were recovered from bacterial samples dried in 10 and 15% than those samples dried in 20 and 25% o AG. For cell viability, samples were tested on day 6. The percent of viable cells remaining after storage in 10, 15, 20 and 25% were 17.3, 17.6, 7.6, and 7.1, respectively. Cell viability for each parameter was tested in triplicate (a=0.05). The greatest amount of viable *E. coli* cells were recovered from samples dried and stored in 15% AG.

Figure 6:
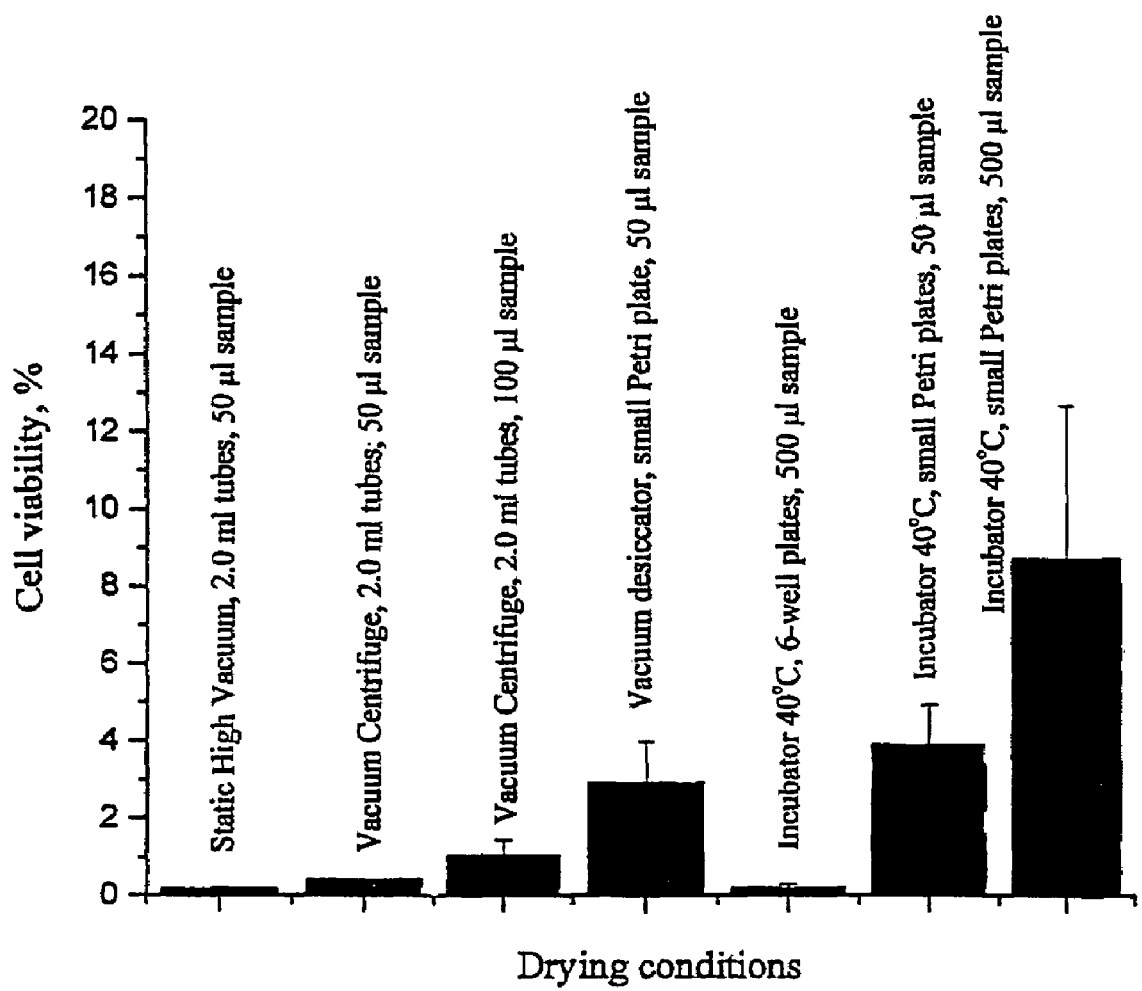
FIG. 6 is a bar graph illustrating cell viability of *E. coli* samples dried in 15% AG at various conditions in accordance with experiment 3 where the x-axis shows various methods of drying, containers, and sample volume, and the y-axis represents % of viable cells recovered after drying.
Figure 7A:
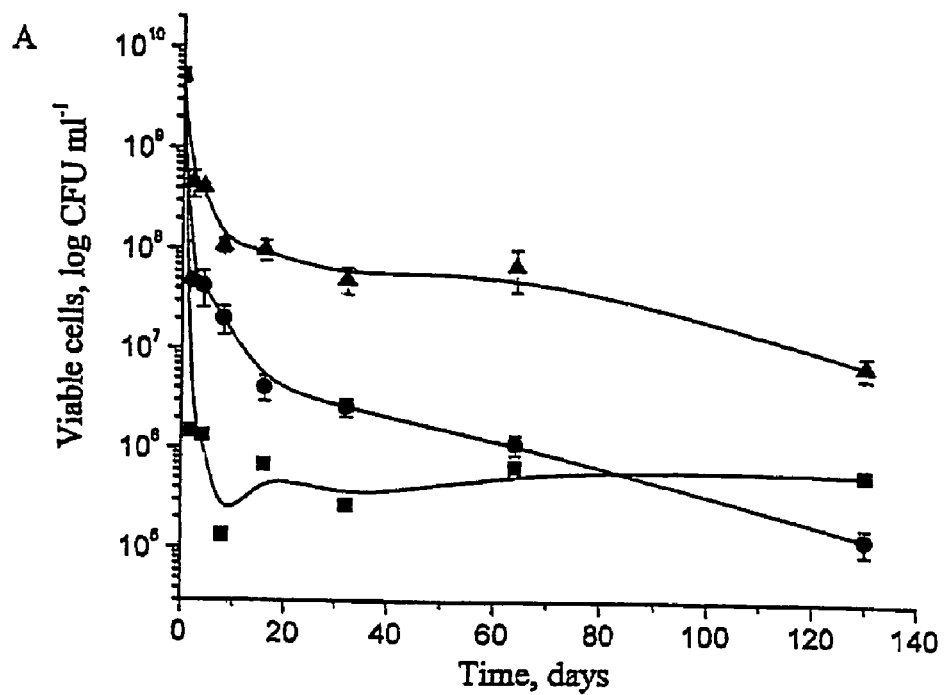
FIGS. 7A-7D are graphs illustrating *E. coli* degradation curves for long-term storage at various temperatures in accordance with experiment 3 where AG (▲), pullulan (●), and PBS (■) samples were stored at 5° C.
Figure 7B:
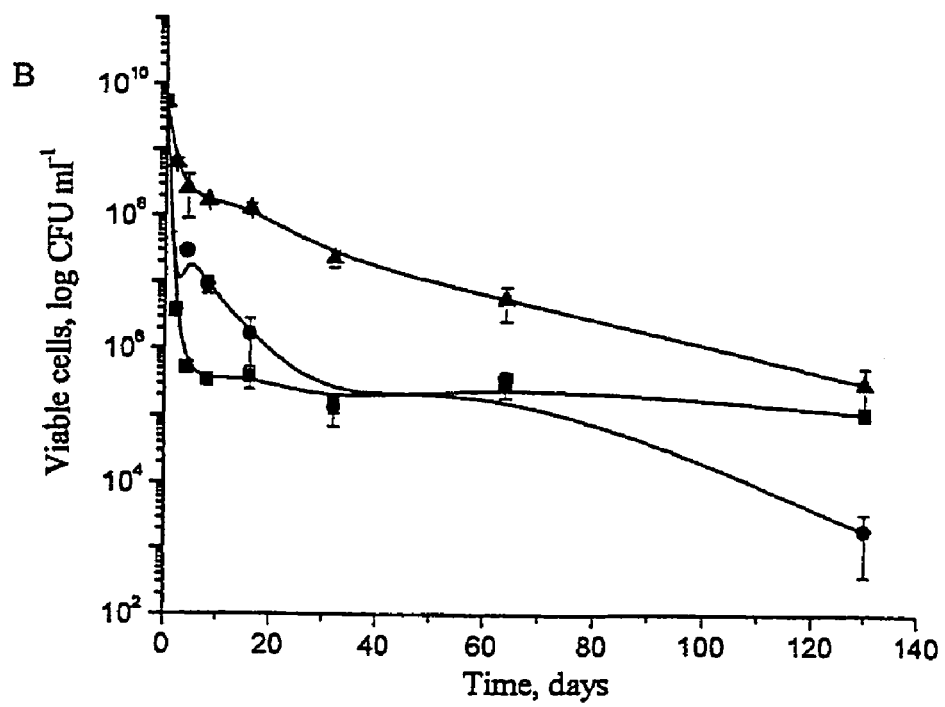
Figure 7C:
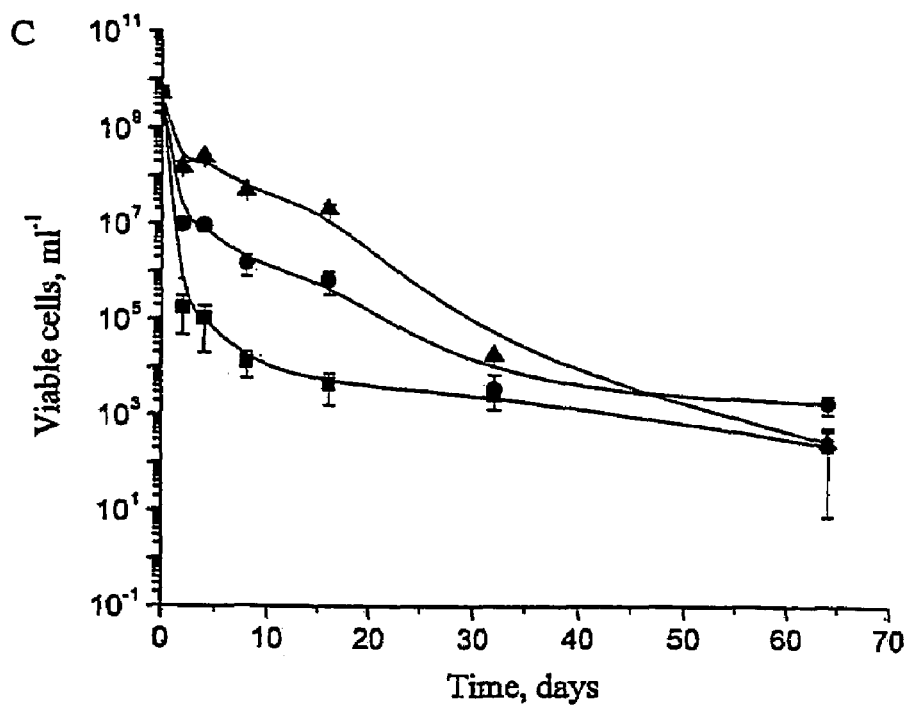
Figure 7D:
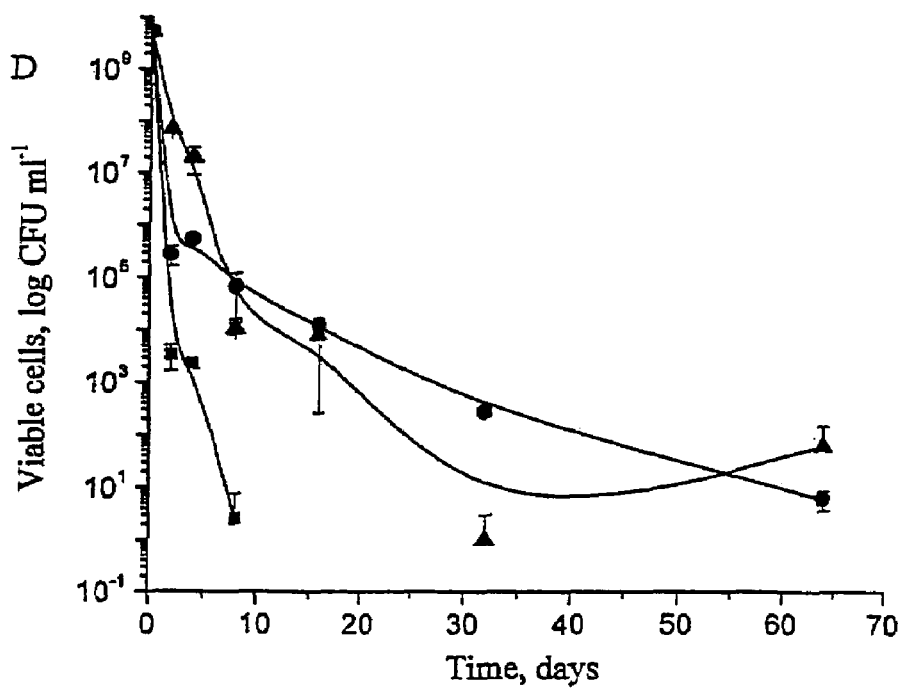
Figure 8A:
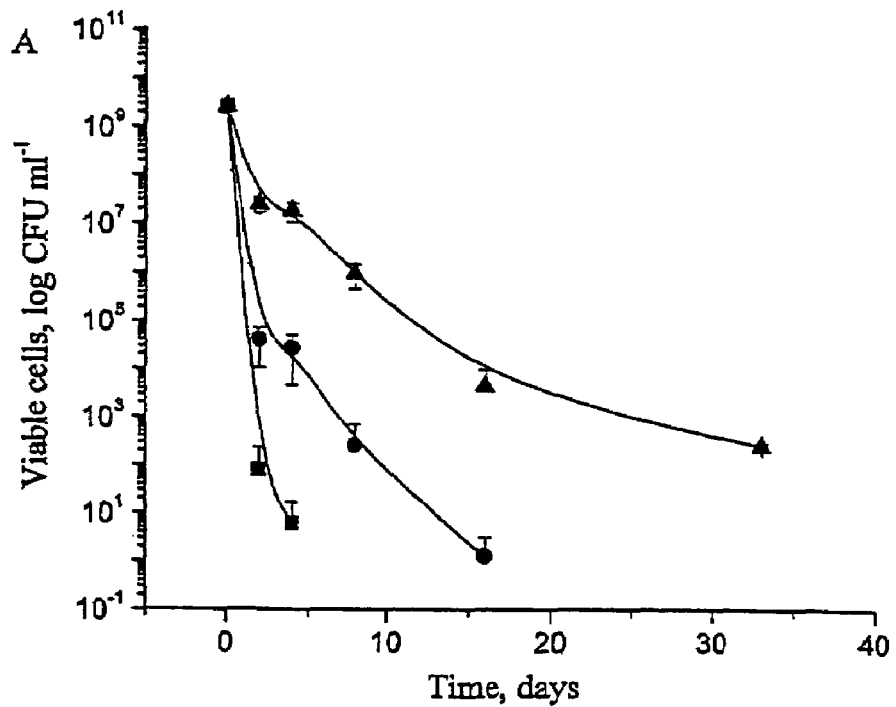
FIGS. 8A-8D are graphs illustrating *E. coli* degradation curves for long-term storage at various humidity in accordance with experiment 3 where AG (▲), pullulan (●), and PBS (■) samples were stored at 46% humidity (FIG. 8A), 53% humidity (FIG. 8B), 76% humidity (FIG. 8C) and 86% humidity (FIG. 8D).
Figure 8B:
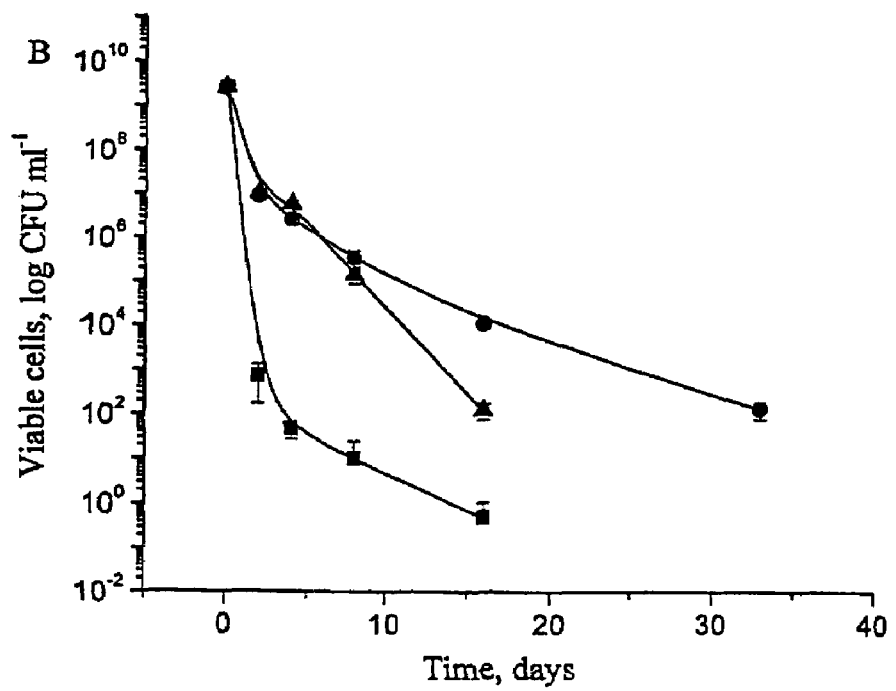
Figure 8C:
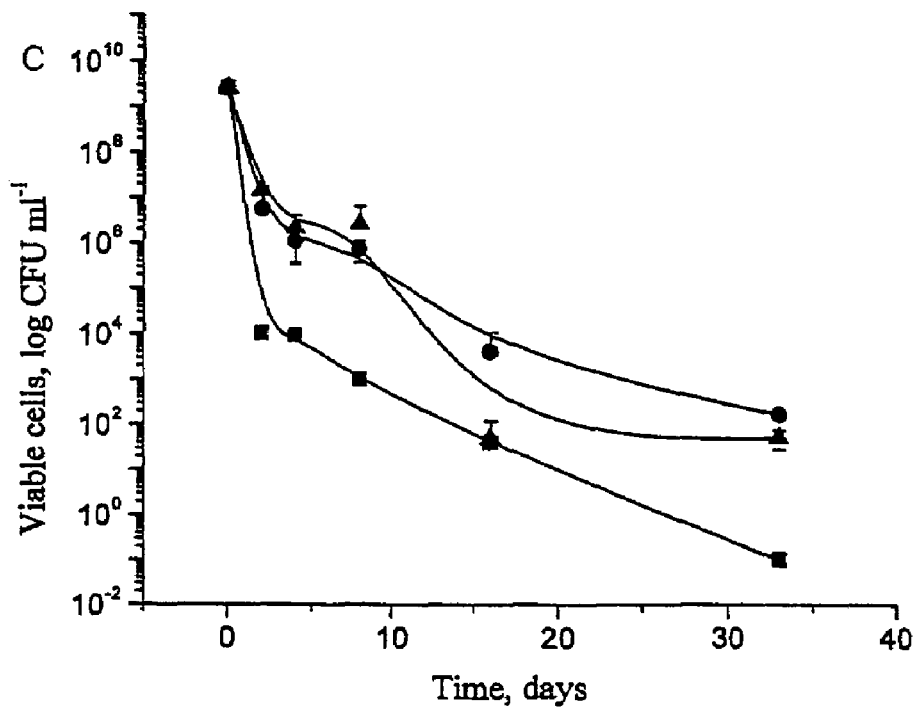
Figure 8D:
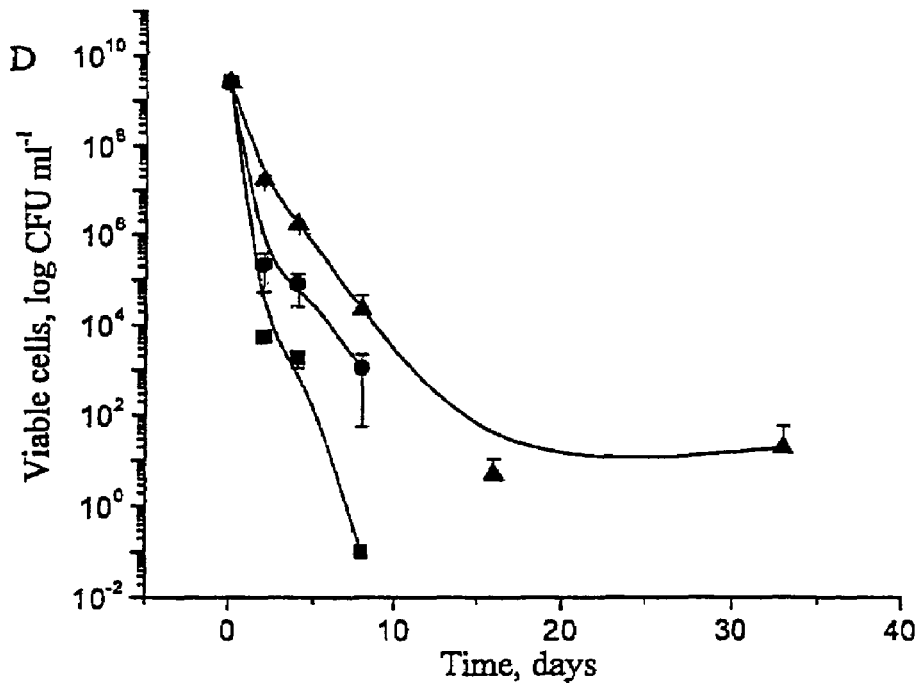

In addition to determining the optimal concentration of AG, several variables were tested in order to find the most favorable container and method of drying *E coli* (for experimental design see Table 2.2). Desirable qualities of the drying method include quick and simple drying procedure, ability to dry many samples simultaneously and maximum recovery of viable cells. The results from several optimization experiments are illustrated in FIG. 6. Since the drying time for each parameter varied, the relative numbers of viable cells recovered after drying were compared. Results from samples dried in 12.5 cm$^2$ culture flasks and glass vials were not presented in FIG. 6 because time to dry exceeded 24 hours, and this was undesirable for the present experiment. Bacterial samples in AG dried under high vacuum at ambient temperature took less than 1 h to dry, but recovered cells were less than 1% of original titer, and there were limitations to the capacity of the static high vacuum machine. Samples that were dried in vacuum centrifuge and desiccator were favorable because the drying time was ~6 h. However, bacterial titers measured after drying were between 1-3% of original titer. Vegetative cell recovered after drying in 6 well plates at 40° C. in a static incubator were less-than 0.5% of the original titer. The best and most consistent results were obtained when *E. coli* samples in AG were dried in small Petri plates at 40° C. in a static air incubator containing silica desiccant.

Vegetative cells recovered from 50 and 500 μl of dried samples in Petri plates were 4.0% and 9.0% of the original titer, respectively. The difference in titers of the varying volumes was likely due to the rate of drying.

Long-Term Preservation of *E. Coli* Cells

To determine survival of bacterial cells after preserving in protective polymers for long-term storage under various conditions, *E. coli* samples in 15% AG, 15% pullulan (control polymer), and PBS (control buffer) were dried at 40° C. After drying, two types of long-term preservation experiments were performed: (1) storage at various temperatures and constant humidity and (2) storage at various humidity and constant temperature. These are referred to from this point forward as temperature and humidity experiments.

For temperature experiments, samples were dried, stored at 5, 15, 25, or 40° C., at constant humidity (~33%) and tested for cell viability on days 2, 4, 8, 16, 32, 64 and 128 of storage. The titers for AG, pullulan and PBS samples after drying were 9.0, 1.0 and 0.03% of original titer, respectively. Bacterial degradation plots for all preserving media and temperatures are shown in FIGS. 7A-7D. All *E. coli* samples exhibited an initial sharp decrease in viability followed by a slower linear decline. The duration of the initial drop appeared to be during drying and the stabilization period that took up to 8 days. Long-term preservation of bacterial cells is described by comparing the loss of viability in the various preserving media and storage temperatures. Bacterial titers for AG, pullulan and PBS were 1, 2 and 3 logs less than original titer (OT) on day 4 when stored at 5° C., respectively. On day 8, bacterial titers obtained from AG, pullulan and PBS samples were 1, 2, and 4 logs less than OT, respectively, when stored at 5° C. Bacterial titers measured from AG samples on subsequent days 16, 32 and 64 appeared to stabilize 31 until the last day for testing. On day 128 when stored at 5° C., *E. coli* samples preserved in pullulan and PBS recovered viable cells 4 logs less than OT, and bacterial titers obtained from testing AG samples were 3 logs less than OT. Similar trends were present when storing samples at 15° C.; however, the rate of bacterial degradation appeared to increase. Bacteria recovered from AG and pullulan samples stored at elevated temperatures 25 and 40° C. remained viable up to day 64. *E. coli* in AG stored at 25 and 40° C. were 270 and 63 CFUml$^{-1}$, respectively. Viable cells in pullulan stored at 25 and 40° C. were 1800 and 6.0 CFUml$^{-1}$, respectively. Whereas, bacteria in PBS rapidly declined to approximately 230 CFUml$^{-1}$ by day 64 at 25° C. and few viable cells were detected by day 8 at 40° C. The low number of viable cells confirms that this strain of bacteria is sensitive to desiccation. The results indicate that AG and pullulan provides adequate protection for *E. coli* cells during desiccation and storage at low temperatures and humidity.

*E. coli* samples stored at various temperatures declined in viability with increasing storage temperature. This linear relationship can be used to estimate the shelf-life of bacteria stored at a particular temperature. Various mathematical models have been employed to extrapolate cell viability of stored bacteria by applying the Arrhenius equation to determine thermal degradation (Greiff and Rightsel, 1965; Barbaree et al., 1982).

Humidity experiments are summarized in degradation curves shown in FIGS. 8A-8D. Viability of *E. coli* preserved in AG and control samples declines steadily for all humidity levels. More viable cells were recovered from AG samples stored in 46% humidity than any other humidity. *E. coli* remained viable up to 32 days in AG when stored at 46, 76, and 86% humidity. The titers for AG samples stored at 46% for 32 days declined by 7 logs from original titer, and no viable bacteria were present in the PBS' and pullulan control samples. AG and PBS samples contained no viable bacteria on day 32 when stored at 53% humidity; whereas, viable bacteria were present in pullulan which was 7 logs less than original titer. The titers for AG and pullulan samples declined 8 and 7 logs on day 32 when stored at 76% humidity, respectively. There were no viable bacteria present in PBS samples. AG samples stored at 86% for 32 days recovered viable bacteria 8 logs less than original titer; whereas, there were no viable bacteria present in pullulan and PBS samples. All samples stored at 76 and 86% humidity were no longer dry because they gained moisture from within their relative humidity chambers by day 32 of testing. There were no viable bacteria recovered from all samples tested on day 64 of storage.

Conclusion

*E. coli* viability varies significantly depending on storage conditions. *E. coli* vegetative cells were best preserved when diluted in 15% AG and dried in small Petri plates in a 40° C. incubator containing silica desiccant for ~20 hours. Long-term storage was optimal when samples were maintained at 5° C. at low humidity. The time to degrade *E. coli* to 100 CFU when stored at 5, 15, 25, and 40° C. are 660, 240, 65, and 20 days, respectively. *E. coli* cells preserved in AG were less sensitive to desiccation than control and retain their viability under cool and dry storage conditions. For extended period of time, *E. coli* cells retain their viability in AG at temperatures and humidity levels of 5-15° C. and 30-46%, respectively.

Experiment 4

Introduction

Experiment 4 focuses on the design and develop a process for long-term preservation of *B. subtilis* at ambient temperature. *B. subtilis* vegetative cells were subjected to a preservation process that promotes spore formation during desiccation. This method involves bacteria suspensions mixed with AG polymer and air dried at 40° C. for about 48 h. The samples were stored at various temperatures and humidity, and tested for viability before and after drying and during storage.

Materials and Methods

*B. Subtilis* Cultivation, Preparation of Concentrated Cell Suspension, and Estimating Cell Viability

*Bacillus subtilis* ATCC 6051 was purchased from ATCC. *B. subtilis* cultures were grown in Difco nutrient broth for 18 hours (beginning of stationary phase) at 200 rmp and 37° C. Bacterial cells were harvested by centrifuging for 7 min at 4,500 rpm and discarding the supernatant. The concentrated cell suspension was prepared by adding 1 ml of PBS to each pellet formed from 50 ml of original culture. Viability of cultures before and after drying and during storage was tested by diluting samples and plating them on nutrient agar.

Spore Staining

To determine the presence of spores, *B. subtilis* suspension before and after drying were smeared onto glass slides and heat fixed. The stains used for this procedure were 5% malachite green oxalate (cat # M-290) and safranin-S (cat # 212534) purchased from Fisher Scientific. The smears were stained as described by Pierce and Leboffe (Pierce 1999). These slides were observed using a bright-field Nikon Eclipse E800M microscope. Pictures were obtained digitally using SPOT V.4.0.4 camera model 2.3.0 V1.0 from Diagnostic Instruments, Inc., Sterling Heights, Mich. The percent of spores produced were determined by counting spores and comparing these numbers to the vegetative cells present in the pictures.

Optimization Experiments

Short-term experiments were performed to determine the optimal conditions for long-term storage of *B. subtilis* samples. The parameters that were optimized included AG concentration, drying temperatures and time, sample volume and containers.

Polymer Concentration Determination Procedure

One part concentrated *B. subtilis* suspension as mixed with four parts of 10, 15, 20 or 25% AG. Five hundred microliters of these *B. subtilis* bacterial suspensions in AG were aliquoted into glass vials purchased from Fisher (cat # 03-338C), The samples were dried uncovered in 40° C. incubator (Lab Line Imperial III Model 302, Fisher, cat # 11-702-10) containing silica desiccant beads for approximately 48 h. Dried samples were covered and stored at 25° C. Bacterial viability was tested as described in Experiment 3 before and after drying and storage on day 11.

Container, Sample Volume and Drying Temperature Determination Procedure

*B. subtilis* bacterial suspensions in 15% AG and PBS were prepared as described above. Container, sample volume, and drying temperature experiments were carried out as described in Experiment 3 using *B. subtilis* bacterial suspensions. Bacterial viability was tested as described in Experiment 3, before and after drying.

Long-Term Storage Experiments for *B. Subtilis* Samples

Based on optimization procedures, the following protocol was used for long-term preservation of *B. subtilis* cells. Bacterial suspensions in 15% AG, 15% pullulan, and PBS were prepared as described above. Bacterial suspensions in 15% pullulan and PBS were used as controls. Glass vials (7.4 ml) were labeled and 500 µl of diluted bacterial suspensions were aliquoted into these vials. The samples were dried uncovered on their sides at 40° C. in a Lab Line Imperial III incubator (Model# 302) containing silica desiccant beads for approximately 48 h.

For temperature experiments, dried samples were sealed and placed into 470 ml square containers. Then, the containers were sealed with paraffin and placed in incubators set at 5, 15, 25, and 40° C. Bacterial viability was tested as described in Experiment 3, before and after drying and after storage on days 2, 8, 16, 32, 64, and 128.

For humidity experiments, un-capped vials containing dried B. subtilis samples were placed in RH chambers. RH chambers contained dried bacterial samples in glass vials and small beakers filled with saturated salt solutions (Table 2.1) to maintain relative humidity. The RH chambers were sealed and stored at 25° C. Bacterial viability was tested as described in Experiment 3, before and after drying and after storage on days 2, 4, 8, 16, 32, 64, and 128.

Results and Discussion

Optimization Experiments for Long-term Preservation of *B. Subtilis*

Numerous drying and short-term storage experiments were conducted to determine the optimal conditions for preserving *B. subtilis* in AG. The parameters that were optimized included concentration of AG, storage containers, drying temperature, method and duration of drying, and storage temperature. A detailed summary of these parameters are shown in Table 2.2. Similar to *E. coli* preservation in Experiment 3, controls for *B. subtilis* experiments were PBS (buffer control) and pullulan (polymer control).

Figure 9:
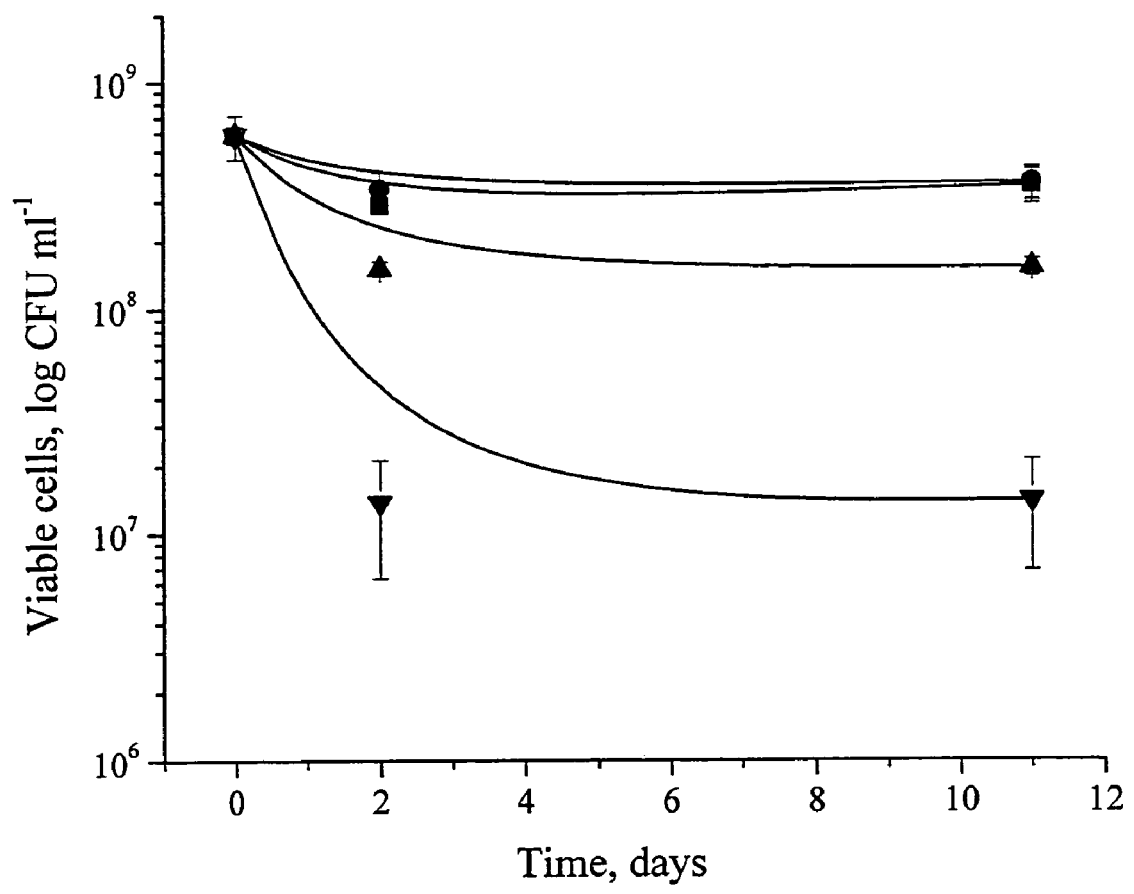
FIG. 9 is a graph illustrating viability of *B. subtilis* cells preserved at various AG concentrations in accordance with experiment 4 where AG was prepared in concentrations of 10% (■), 15% (●), 20% (▲), and 25% (▼).

Determining the optimal concentration of AG for preserving *B. subtilis* was accomplished by testing bacterial viability after samples were dried and stored for 11 days in various concentrations of polymer ranging from 10 to 25%. Viability curves for *B. subtilis* in all concentrations of AG are shown n FIG. 9. After drying in glass vials, the percent of viable cells of *B. subtilis* samples remaining in 10, 15, 20, 25% AG was 49.0, 57.8, 25.8, and 2.3%, respectively. By day 11 of storage at 25° C., the percent of viable cells preserved in 10, 15, 20, 25% AG was 59.7, 61.4, 25.9, 2.4%, respectively. Similar to *E. coli*, more viable cells were recovered from *B. subtilis* samples dried in 15% AG.

Figure 10:
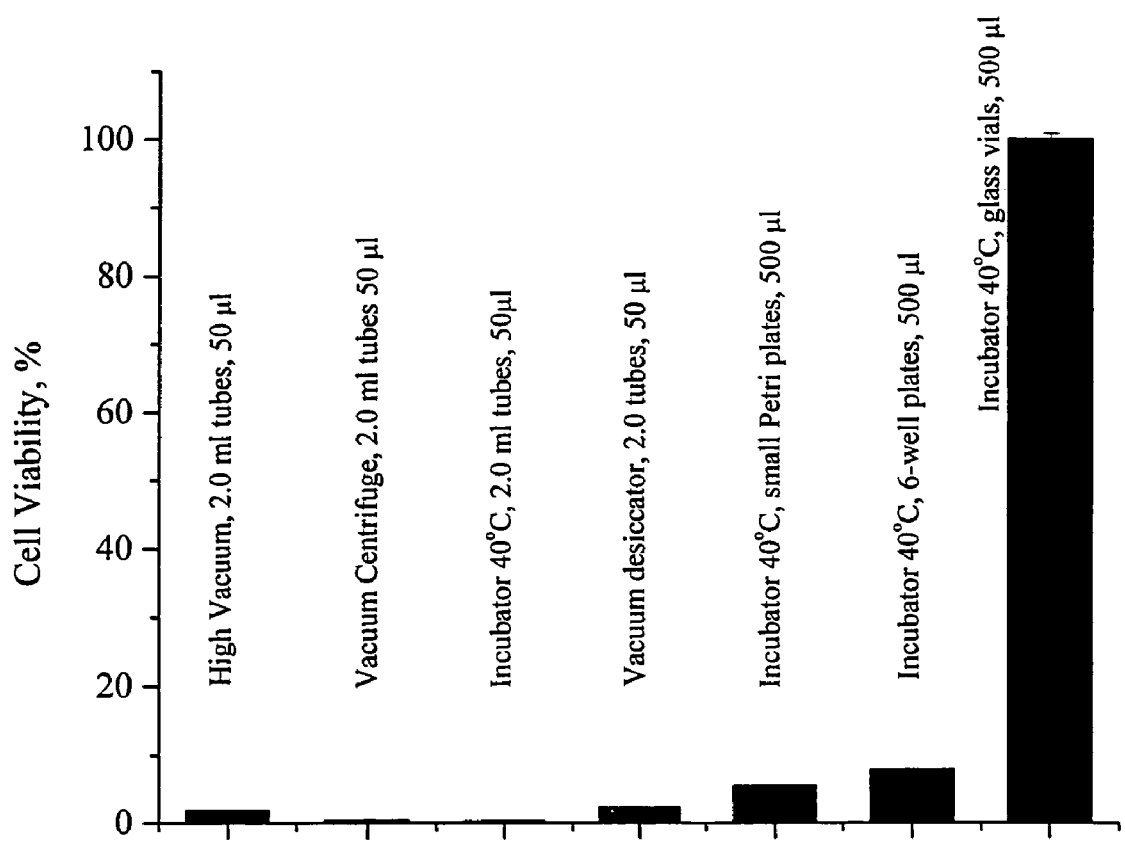
FIG. 10 is a bar graph illustrating cell viability of *B. subtilis* samples dried in 15% AG at various conditions in accordance with experiment 4 where the x-axis shows various methods of drying, containers, and sample volume and the y-axis represents % of viable cells recovered after drying.
Figure 11A:
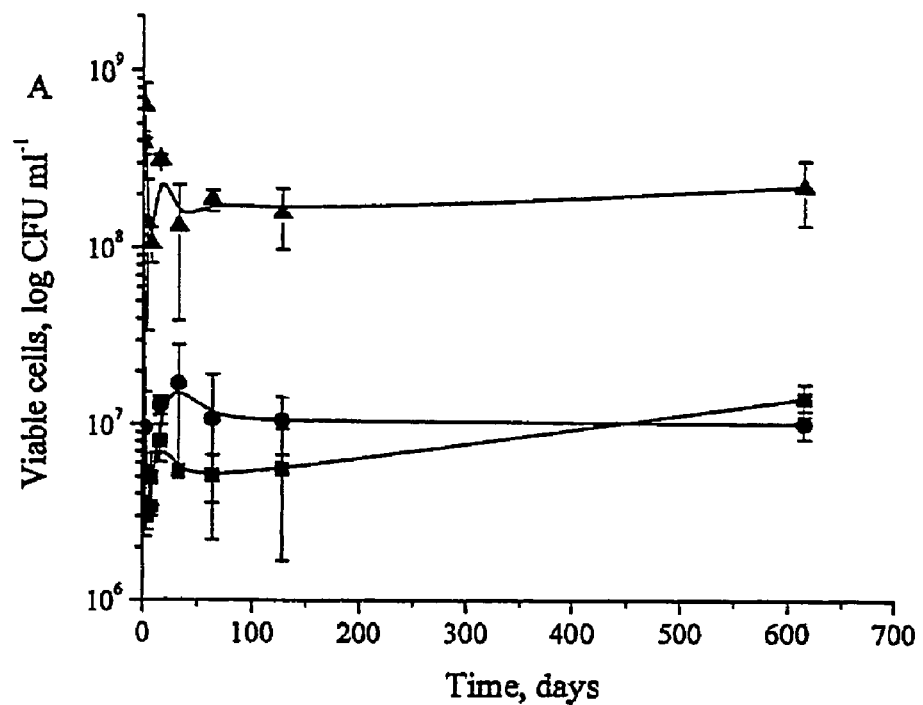
FIGS. 11A-11D are graphs illustrating *B. subtilis* degradation curves for long-term storage at various temperatures in accordance with experiment 4 where AG (▲), pullulan (●), and PBS (■) samples were stored at 5°C.
Figure 11B:
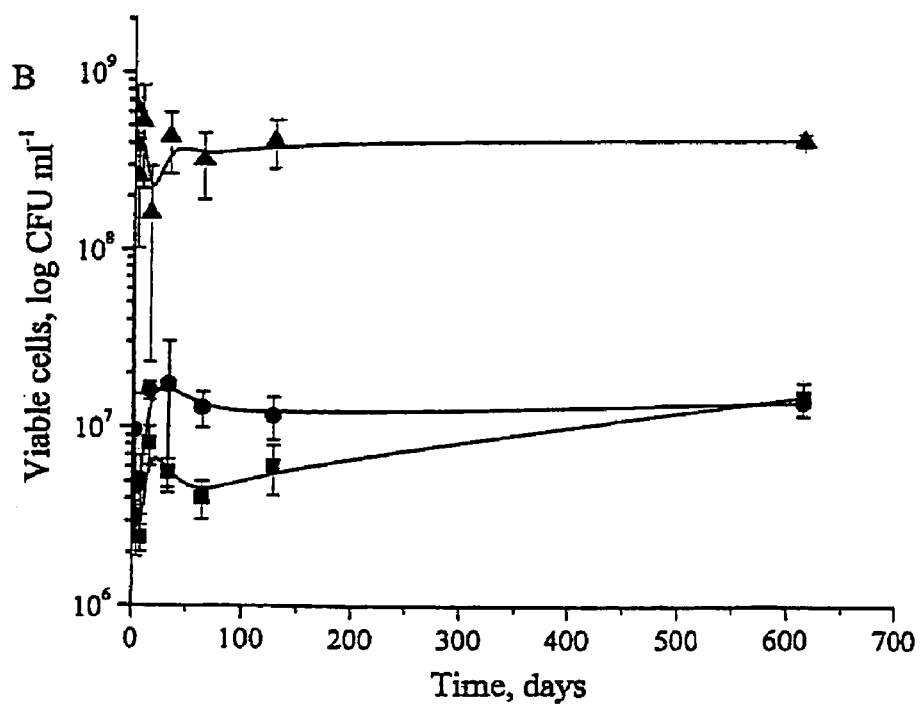
Figure 11C:
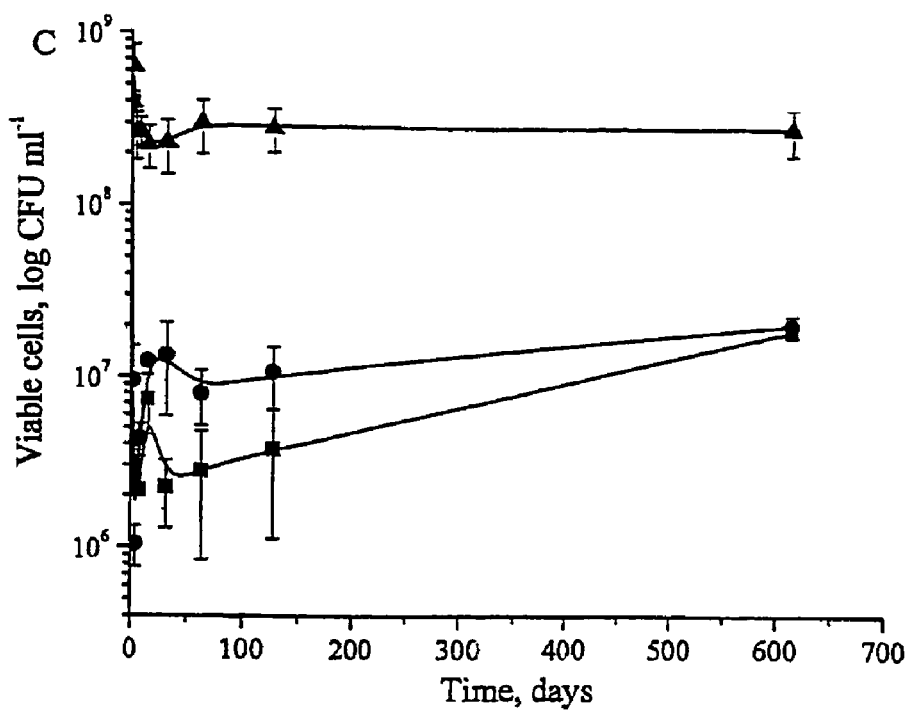
Figure 11D:
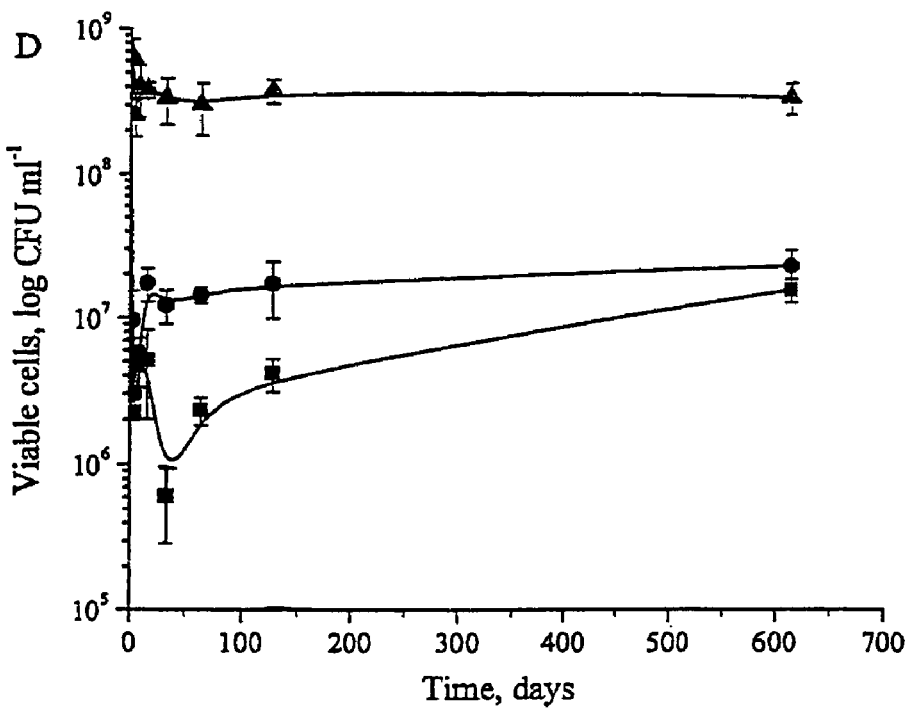
Figure 12A:
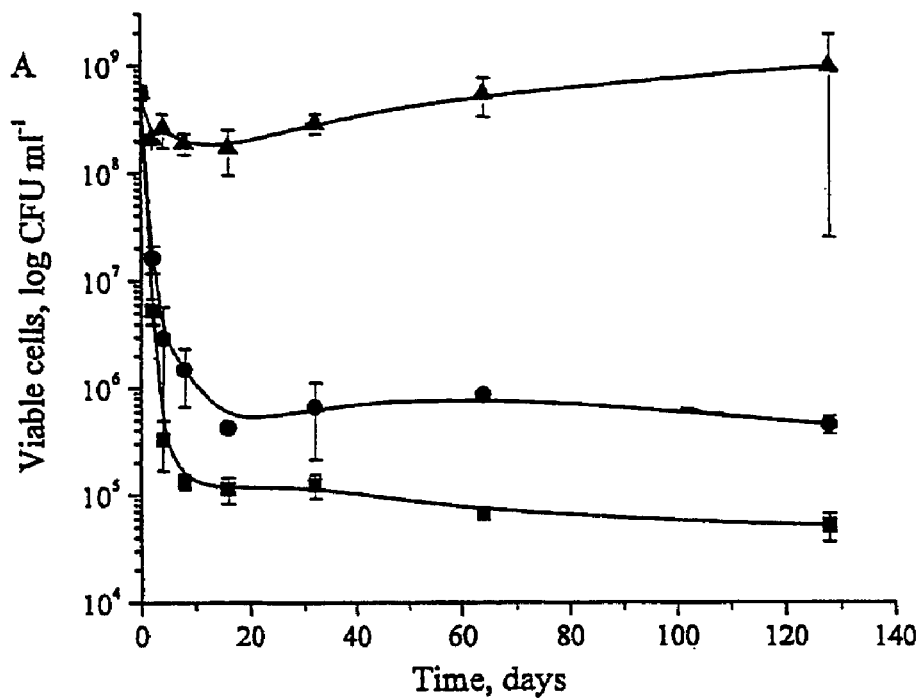
FIGS. 12A-12D are graphs illustrating *B.* subtilis degradation curves for long-term storage at various humidity in accordance with experiment 4 where AG (▲), pullulan (●), and PBS (■) samples were stored at 46% humidity (FIG. 12A), 53% humidity (FIG. 12B), 76% humidity (FIG. 12C) and 86% humidity (FIG. 12D).
Figure 12B:
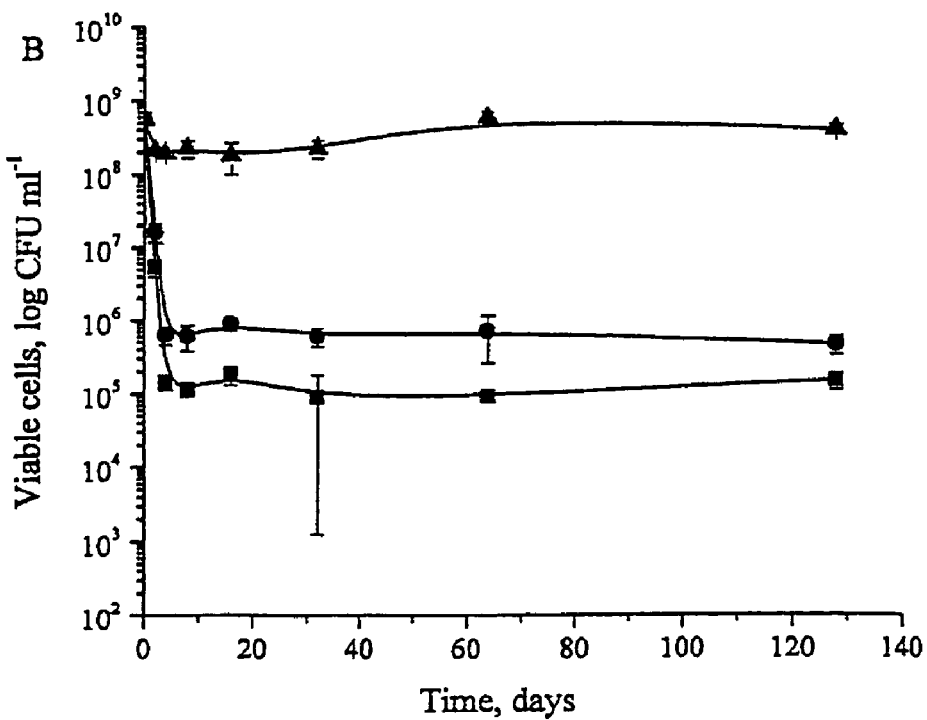
Figure 12C:
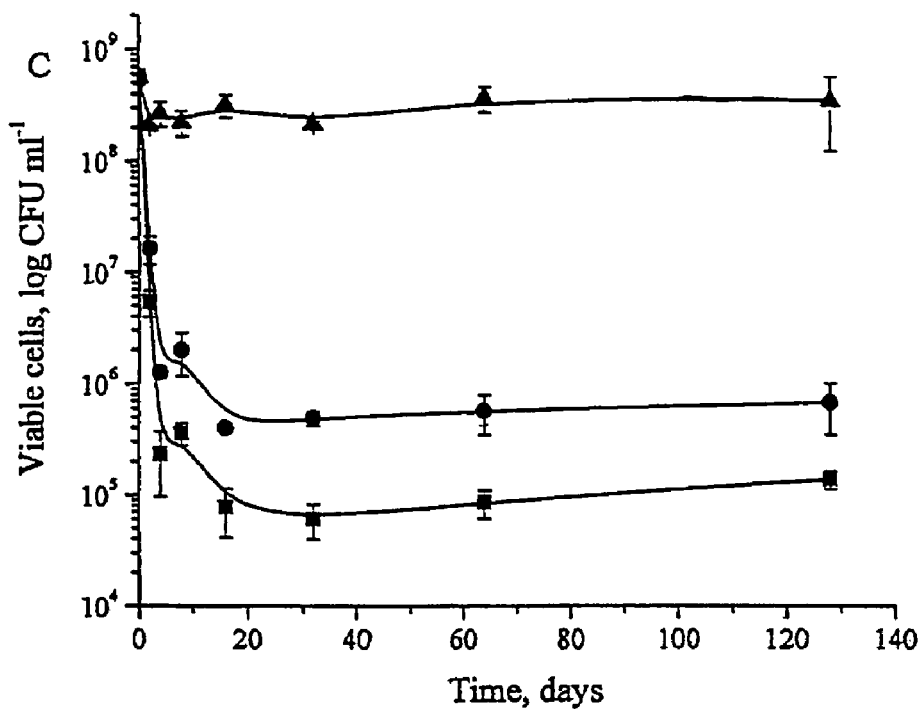
Figure 12D:
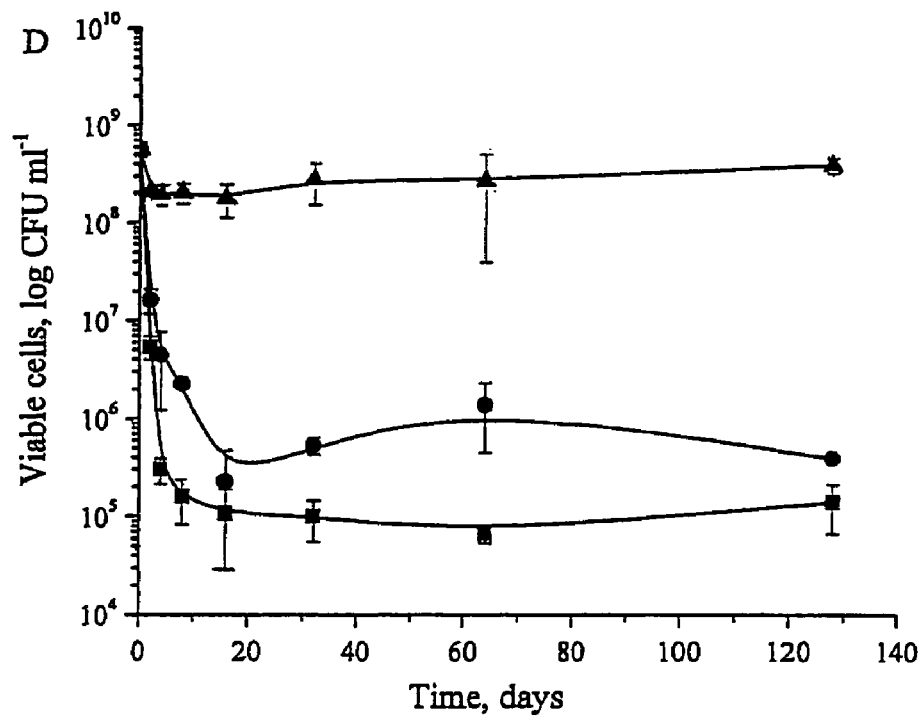

Several parameters were tested to determine the optimal container and drying method for preserving *B. subtilis*. Desirable qualities of the drying method include simple drying procedure that would maximize the number of viable cells recovered. The results from these experiments are shown in FIG. 10. Bacterial samples dried under static high vacuum, vacuum centrifuge, low vacuum desiccator and incubator in 2.0 ml tulles were less than 3.0% viable. In addition, bacterial cultures dried in small Petri plates and 6-well plates at 40° C. recovered 5.5 and 7.8% of viable cells, respectively. The viability of bacterial samples in AG and dried in glass vials for 48 h at 40° C. was ~100%. This was indicated by colonies formed from these samples after drying and reconstitution in water. The optimal parameters for recovering *B. subtilis* from 15% AG were determined to be drying cell suspensions in glass vials for 48 hr in 40° C. incubator containing silica desiccant. The high viability of *B. subtilis* cultures after drying for 48 h implied that, spore formation was probable. Spore staining was performed before and after drying in AG. Vegetative cells produced 99% of free spores after 48 hr of drying. Drying *B. subtilis* vegetative cells in glass vials for 48 hr at 40° C. produced viable spores.

Long-Term Preservation of *B. Subtilis*

*B. subtilis* samples were dried in 15% AG, 15% pullulan (control polymer) and PBS (control buffer) at 40° C. for 48 hr to determine the viability of cells during long-term preservation under various conditions. There were two types of experiments performed:

(1) storage at various temperatures and constant humidity and (2) storage at various humidity and constant temperature. From this point forward, these experiments are referred to as temperature and humidity experiments. For both types of experiments, *B. subtilis* vegetative cells were mixed with 15% AG, placed into glass vials and dried for 48 h at 40° C. There was no significant loss of bacterial viability of cells dried in AG (~100%); whereas, bacterial viability of *B. subtilis* cells dried in pullulan and PBS were two logs less than original titer (OT).

For temperature experiments, vials containing dried samples were sealed and stored at various temperatures (5, 15, 25 and 40° C.) and constant humidity (~33%). Viability curves for *B. subtilis* stored at, various temperatures are shown in FIGS. 11A-11D. After drying for 48 hr, spores were stabilized, and there was no significant decline in bacterial titer up to 128 days of storage for all samples. The experiment was extended to 615 days where the viability of *B. subtilis* spores remained consistent with the titer obtained after drying. The percent of viable *B. subtilis* cells recovered from AG on day 615 when stored at 5, 15, 25, 40° C. was 55.9, 106.3, 69.5, and 86.8, respectively.

*B. subtilis* samples were subjected to 46, 53, 76 and 86% humidity at constant temperature (25° C.) for 128 days of storage. Humidity experiments are summarized in viability curves shown in FIGS. 12A-12D. Initially, more viable cells were recovered from AG samples than pullulan and PBS after drying; however, the viability of *B. subtilis* cells remained steady for all humidity levels up to 128 days.

Conclusions

*B. subtilis* is optimally recovered when suspended in AG and dried for 2 days in glass at 40° C. Bacterial titer in PBS and pullulan controls after drying are 100 fold less than bacterial titer in AG. *B. subtilis* vegetative cells form spores during the 2 day drying process. For both temperature and humidity experiments, *B. subtilis* viability remains consistent after spores are formed. AG provides better environment for spore formation than pullulan and PBS. *B. subtilis* cultures were successfully reserved in AG polymer up to 615 days.

Experiment 5

Introduction

The main focus of Experiment 5 was to design and develop a process for long-term preservation of DNA at ambient temperatures. Two types of DNA were subjected to a drying process in AG and pullulan in order to determine the protective capacity of these polymers. This method involves DNA in TE buffer mixed with AG and pullulan polymer and dried under vacuum for 48 h at room temperature. The samples were stored at various temperatures and humidity, and tested for viability before and after drying and during storage.

Materials and Methods

Isolation of ssDNA ssDNA was isolated from cultured fd-tet phage (generous gift from Dr. Petrenko, Department of Pathobiology, College of Veterinary Medicine, Auburn University, Auburn, Ala.) using a DNA purification method described in Molecular Cloning: a laboratory manual (Sambrook, Fritsch et al. 1989). Five milliliters of cultured phage was placed into a 15 ml polypropolene tube with 5 ml of phenol. This was mixed for a 5 min and the phenol layer was discarded. Another 5 ml of phenol was added for 5 minutes and discarded. Then, 5 ml of phenol-chloroform was added for 5 min and discarded. Then, 5 ml of chloroform was added and discarded. The water layer was transferred into two 50 ml centrifuge tube and the volume level was adjusted to 5 ml with TE buffer. Then, 0.5 ml of NaOAc and 12.5 ml of 100% ethanol was added to each tube. This mixture results in precipitation of ssDNA. This pellet underwent a series of rising steps with ethanol and a final drying overnight in sterile environment. The dried ssDNA was reconstituted in TE buffer which results in a purified ssDNA in TE buffer. The concentration of ssDNA was measured using Shimadzu UV 160U spectrophotometer (Shimadzu Corporation, Japan) at λ 260 nm. Once concentration was known, ssDNA were diluted with TE buffer to 40 ng/µl.

Isolation of dsDNA

Fd-tet phage dsDNA was isolated from infected *Escherichia coli* K91 BKan culture according to protocol 15-8 in Phage Display (Barbas 2001) with the following modification. In step 4, 4 ml of freshly prepared solution of lysozym (10 mg/ml in 10 m/ml Tris HCL [pH 8.0]) was added after the buffered glucose; this modification was derived from Molecular Cloning: a laboratory manual lysis by alkali plasmid vector protocol (Sambrook, Fritsch et al. 1989). After extraction, the dsDNA pellet was reconstituted in TE buffer. The concentration dsDNA were measured using Shimadzu was diluted with TE buffer to 30 ng/µl.

Electrophoresis of DNA in AG Samples ssDNA in the amounts of 200 and 400 ng was measured into 10 µl of 10% AG or TE buffer. Each of these mixtures was combined with 2 µl of 70/75 bromophenol blue (BPB) loading dye. One percent DNA Grade agarose gels containing 20 wells were prepared as follows: 0.7 g of Agarose DNA Grade (Fisher cat # BP164) was added to 70 ml 1×-Tris-borate-EDTA buffer (TBE buffer) (TBE 5× stock: 0.5M Tris, 0.5 M boric acid, 10 mM EDTA), the mixture was heated in a microwave until aga dissolved, and the warm mixture was poured into a gel case with a 20 well comb. To these 1% gels, ssDNA samples containing BPB dye were loaded. Gels were run at 50 V for 2 h in TBE buffer. Gels were stained with SYBR® Green I nucleic acid gel stain (Cambrex Bio Science Rockland Inc., Rockland, Minn., purchased from Fisher cat # BMA 50513) for 1 h. The gels were illuminated using a transilluminator DR-190M (Clare Chemical Research, Dolores, Colo.). Pictures of the stained gels were taken using Kodak EDAS 290 (Eastman Kodak Company, New Haven, Conn.).

Recovery of DNA from AG and Pullulan Polymers

Two kits were tested for DNA recovery from AG and pullulan: (1) GeneClean® Turbo for PCR kit (using the protocol for Rapid Isolation of 0.1-300 kb DNA from solution purchased from Q-Biogene (Carlsbad, Calif.) and (2) QIAquick gel extraction kit from QIAGEN (Valencia, Calif.). Samples were prepared by mixing 200 ng of ssDNA in 50 µl of TE buffer, 10% AG or 10% pullulan. Then, these samples were purified one or the other kit. Since the volume of the recovered DNA samples was too much to load into the wells of the agarose gels, the purified samples were concentrated. The recovered samples were placed in vacuum centrifuge until dry (~3 h). The dried samples were reconstituted with 10 pl of sterile water for 10 minutes. Then, 2 µl of 70/75 bromophenol blue (BPB) loading dye were added to each sample. The samples were loaded into agarose gels and electrophoresis was carried out as described herein.

Polymer Concentration and Drying Temperature Optimization

To determine the optimal concentration of AG, one part of ssDNA in TE buffer was mixed gently with four parts of 10, 15, 20 or 25% AG or TE buffer. Fifty microliters of prepared DNA mixtures were aliquoted into 2 ml polypropolene microcentrifuge tubes (Fisher cat # 05-408-141). These samples were dried uncovered in a vacuum desiccator containing silica gel desiccant at ambient, temperature for ~2 days. The samples were reconstituted in 50 µl of sterile water for 10 minutes and purified using GeneClean® Turbo for PCR kit. The DNA samples recovered from AG were concentrated as described in section 5.2.4 and tested for integrity via electrophoresis as described in section 5.2.3.

To determine optimal drying temperature, ssDNA samples were prepared in 10% AG and TE buffer as abovementioned. These samples were dried in a vacuum desiccator at ambient temperature for 2 days or dried in a static incubator at 40° C. for 24 h. After drying, the samples were reconstituted, purified, concentrated and tested for integrity via gel electrophoresis as described above.

Long-Term Storage Experiments

Based on optimization experiments, the following protocol was used for long-term preservation of ssDNA and dsDNA. One part of ssDNA or dsDNA was prepared in four parts of 10% AG, 10% pullulan or TE buffer. Aliquots of 50 µl were measured into 2 ml centrifuge tubes. AG and pullulan samples were dried uncovered in a vacuum desiccator containing silica desiccant at ambient temperature for 2 days. As a reference, DNA samples in TE buffer were sealed and stored at −20° C.

For temperature experiments, DNA samples dried in AG and pullulan were sealed and placed into containers as shown in FIG. 2.1 C. These containers were placed in incubators set at 5, 15, 25, and 40° C. DNA integrity was tested after drying and after storage on days 2, 4, 8, 16, 32, 64 and 128. For humidity experiments, DNA samples dried AG and pullulan were placed into relative humidity (RH) chambers unsealed. In analogy to temperature experiments, DNA integrity was tested after drying and after storage on days 2, 4, 8, 16, 32, 64 and 128.

Testing DNA Integrity Using Gel Electrophoresis

On testing days, both ssDNA and dsDNA dried in AG and pullulan were . reconstituted with 50 µl of sterile water for 10 min. Reference samples stored at −20° C. were unthawed. All samples (including reference samples) were purified using GeneClean® Turbo for PCR kit. After purification, samples were dried in a vacuum centrifuge for ~3 h or until dry. Then each sample was reconstituted in 10 ul of TE buffer for 10 min and 2 µl of BPB loading dye were added.

For ssDNA samples, 1% agarose gels were prepared using 1×TBE. Samples were loaded into wells and gels were run at 50 V for 2 h in TBE buffer. For dsDNA samples, 0.8% agarose gels were prepared using 4× GBB buffer (GBB 40× stock: 1.68 M Tris, 0.80 M sodium acetate, 72 mM EDTA). Lambda DNA-BstEII digest was used for the molecular weight standard (generous gift from Dr. Petrenko). Experimental samples and molecular weight standards were loaded into wells and gels were run at 50 V for 1.5 h.

All gels were stained with SYBR® Green I nucleic acid gel stain for 1 hour. Gel pictures were taken using Kodak EDAS 290. The relative amount of DNA was determined using Kodak 1D version 3.6 software. DNA integrity was expressed as P percent of intact DNA relative to control DNA stored at −20° C. in TE buffer.

PCR Amplification of ssDNA Recovered from AG and Pullulan Samples

PCR reaction was prepared using dNTP mixture (dNTP set purchased from Amersham Biosciences Piscataway, N.J. cat. #27-2035-01), F8 sense and F8 anti-sense primers (generous gift from Dr. Petrenko) and Taq polymerase (Promega Madison, Wis. Cat # M1661). The concentration of ssDNA from experimental samples was unknown. The concentration of the positive control was 40 ng/gl of ssDNA stored in TE buffer at 20° C. The thermocycler was programmed as follows: 94° C. for 3 min followed by 35 cycles: 94° C. for 10 s, 46° C. for 20 s, and 72° C. for 45 s; 72° C. for 4 min. The reaction mixtures was dropped to 4° C. until samples were tested'further. After the reaction was completed, the samples were loaded into gels as described in section 5.2.3.

PCR products were sequenced at the Auburn Genomics and Sequencing Laboratory (Auburn University, Auburn, Ala.) using S20 primer. The sequences were analyzed using Chromas 1.45 (Technelysium Pty. Ltd, Tewantin Qld 4565, Australia) and DNAstar (Madison, Wis.) programs.

Results and Discussion

Optimization Experiments for Long-term Preservation of ssDNA ssDNA was used to determine optimal parameters for long-term preservation for both types of DNA. Because ssDNA is less stable and more susceptible to degradation than dsDNA, the optimal conditions for ssDNA would apply to dsDNA. Several experiments were conducted to determine the best method for DNA recovery from AG because DNA did not migrate under electrical current in the presence of AG. Two methods were tested to optimize recovery of DNA from AG. QIAquick gel extraction and GeneClean® Turbo kits were compared. DNA was successfully purified from AG samples using both methods; however GeneClean® Turbo kit appeared to recover more DNA, so this method was used from this point forward.

A number of experiments were performed to determine the optimal AC concentration and drying temperature for long-term preservation of DNA. ssDNA was dried in 10, 15, 20 and 25% AG, reconstituted in water and tested via gel electrophoresis. More ssDNA was recovered from decreasing concentrations of AG, so the most favorable AG concentration for ssDNA preservation was determined to be 10%. Drying temperatures tested were 25° C. and 40° C. The optimal drying temperature for DNA samples in AG was determined to be 25° C. because more DNA was detected.

Long-Term Preservation of ssDNA

To determine integrity of ssDNA after preserving in protective polymers for long -term storage under various conditions, ssDNA samples in 10% AG and 10% pullulan (control polymer) were dried at 25° C. After drying, two types of long-term preservation experiments were performed: (1) storage at various temperatures and constant humidity and (2) storage at various humidity and constant temperature. These are referred to from this point forward as temperature and humidity experiments.

Figure 13A:
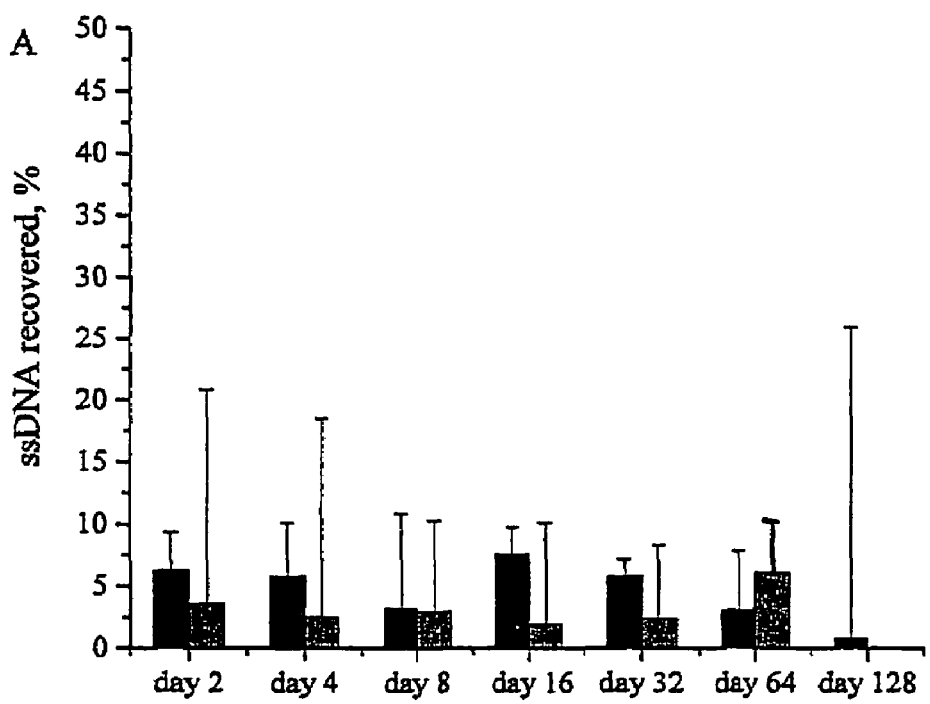
FIGS. 13A-13D are graphs illustrating the amounts of intact ssDNA recovered from AG (black bars) and pullulan (gray bars) that were stored at various temperatures in accordance with experiment 5 where samples were stored at 5° C.
Figure 13B:
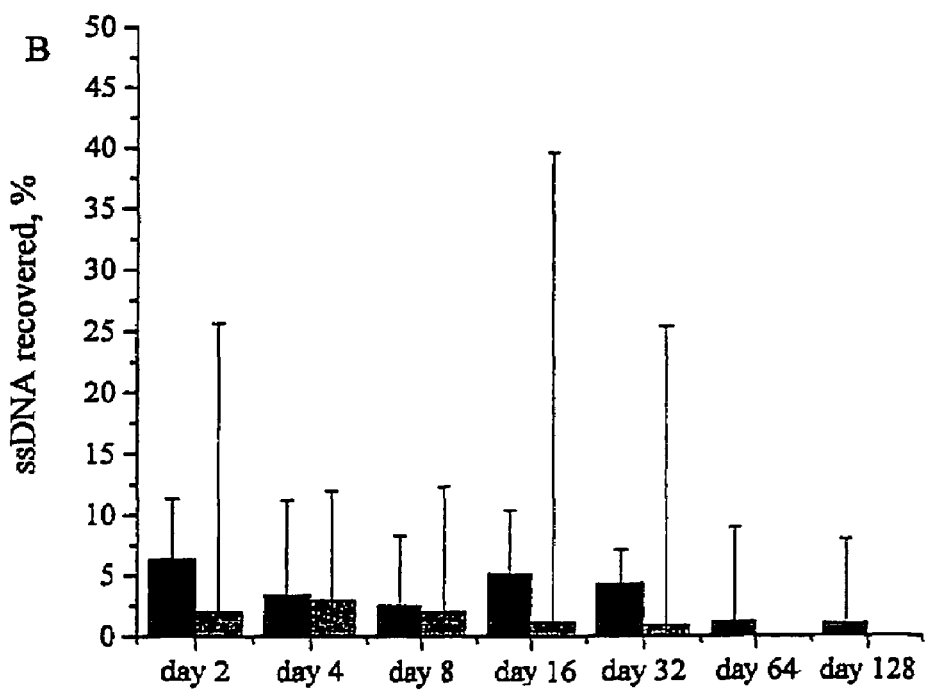
Figure 13C:
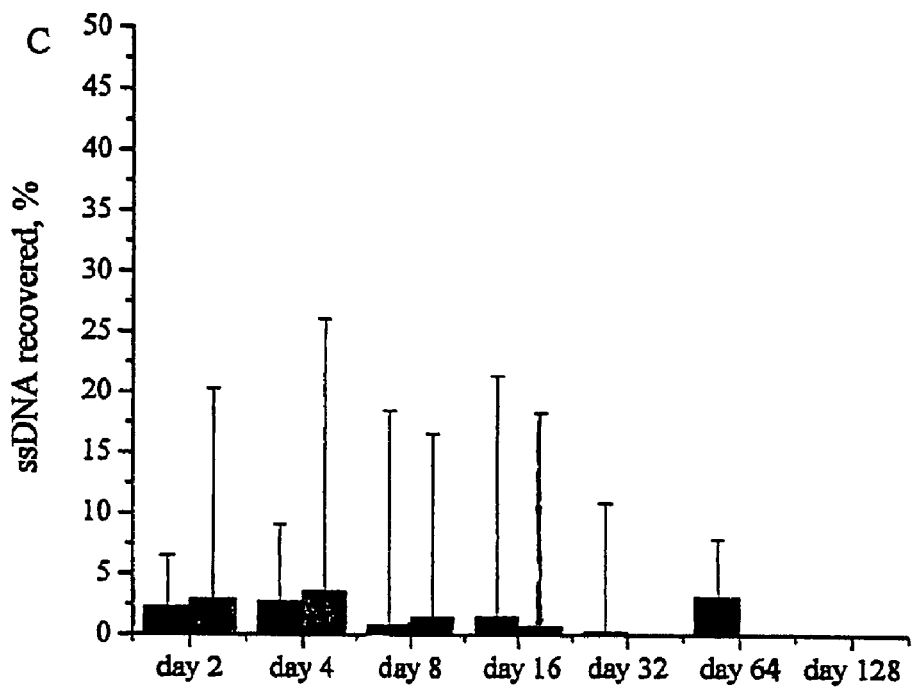
Figure 13D:
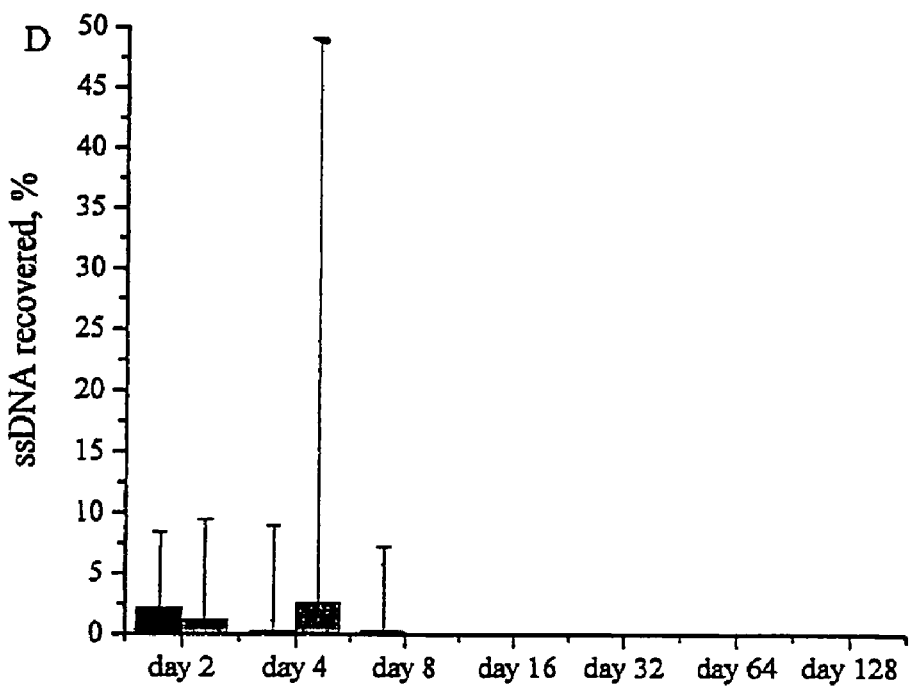
Figure 14A:
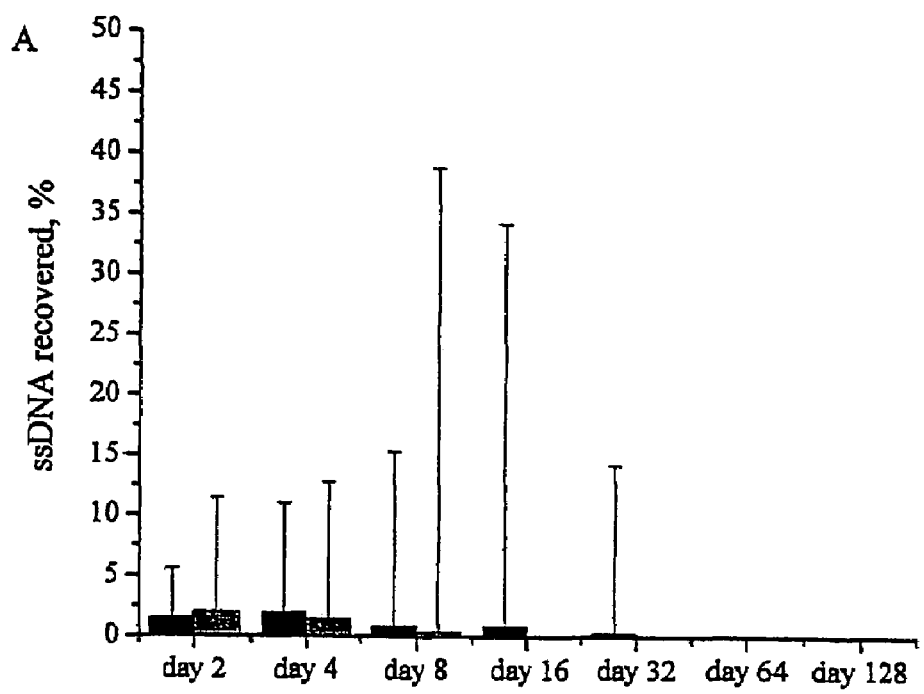
FIGS. 14A-14D are graphs illustrating amounts of intact ssDNA recovered from AG (black bars) and pullulan (gray bars) that were stored at various humidity in accordance with experiment 5 where samples were stored at 46% humidity (FIG. 14A), 53% humidity (FIG. 14B), 76% humidity (FIG. 14C) and 86% humidity (FIG. 14D).
Figure 14B:
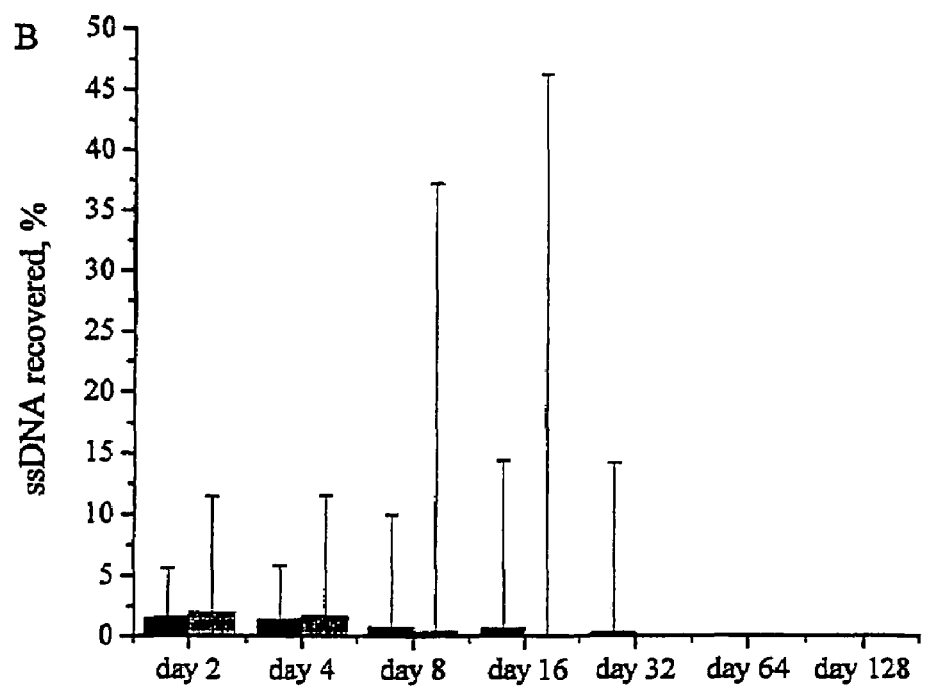
Figure 14C:
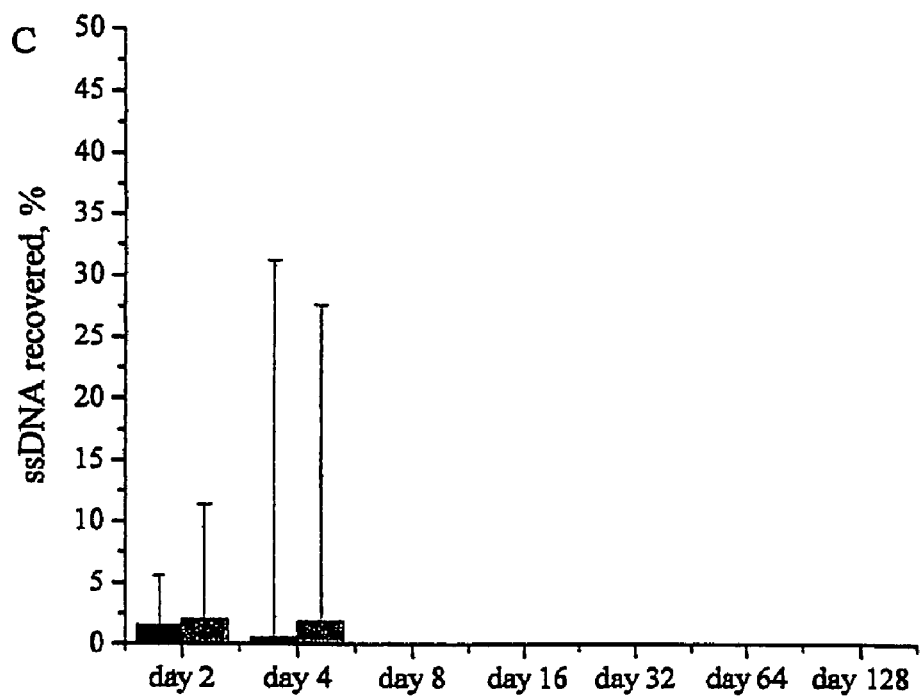
Figure 14D:
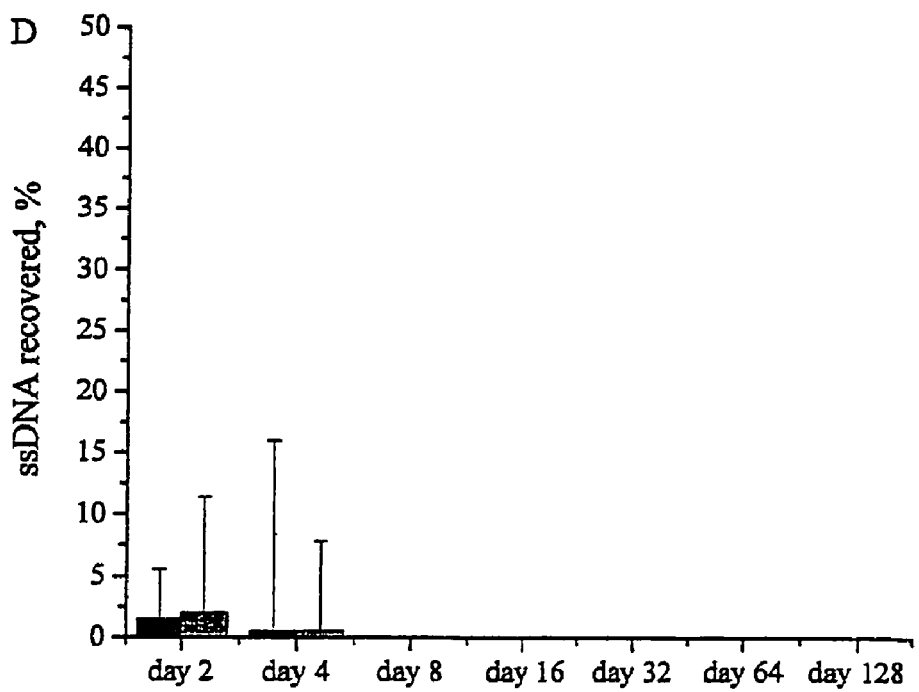

For temperature experiments, samples were dried, stored at 5, 15, 25, or 40° C. an constant humidity (~33%) and DNA integrity was tested on days 2, 4, 8, 16, 32, 64 and 128 of storage. The relative amounts of ssDNA recovered from AG samples stored at 5, 15, 25, and 40° C. and tested on day two of the experiment were 6.3, 6.3, 2.3, and 2.2%, respectively (FIGS. 13A-13D). The relative amounts of ssDNA recovered from pullulan samples stored at 5, 15, 25, and 40° C. and tested on day two of the experiment were 3.6, 2.0, 2.9, and 1.2%, respectively (FIGS. 13A-13D). Intact ssDNA was detectable up to day 128 for AG samples stored at 5 and 15° C. (FIGS. 13A-13B). ssDNA dried in AG was undetectable on day 128 and day 8 when stored at 25 and 40° C., respectively (FIGS. 13C-13D). For pullulan samples, ssDNA was detectable up to day 64, 32, 16, and 4 when stored at 5, 15, 25, and 40° C., respectively. In humidity experiments, ssDNA integrity diminished rapidly. For AG samples, ssDNA was visible up to day 32 when stored at 46 and 53% humidity (FIGS. 14A-14B), and day 4 when stored at 76 and 86% humidity (FIGS. 14C-14D). For pullulan samples, ssDNA was detected up to day 8 when stored at 46 and 53% humidity (FIGS. 14A-14B) and up to day 4 for samples stored at 76 and 86% (FIGS. 14C-14D).

DNA Integrity Tested by PCR Amplification and Sequencing of AG and Pullulan Samples ssDNA samples stored at various temperatures (5, 15, 25, 40° C.) were tested on day 118 to determine whether the remaining ssDNA were able to produce PCR products. In one set of experiments, AG and pullulan samples were purified from polymers using Gene Clean® Turbo Kit for PCR according to manufacturer's protocol. In addition, samples stored at 25° C. for 118 days were tested to determine if samples could successfully undergo a PCR reaction without prior purification from AG and pullulan polymers.

In spite of the little amount or even absence of intact ssDNA present in AG samples stored at various temperatures detected via gel electrophoresis, the samples produced PCR products of correct size and were successfully sequenced with no variation in ssDNA sequence compared to control. Pullulan samples were barely visible in the electrophoretic image but sequencing results indicate that there was no variation in DNA sequence compared to control. AG samples were also tested to determine if they could undergo PCR reaction in the presence of AG or pullulan. The entire pellet of dried AG or pullulan samples stored at 25° C. for 118 days were placed into the PCR tube with reaction components. The PCR reactions were successful and DNA sequencing indicated that in the presence of ~6% AG and pullulan there was no variation in DNA sequence of the PCR products compared to control DNA samples stored at −20° C.

Long-Term Preservation of dsDNA

To determine integrity of dsDNA after preserving in protective polymers for long-term storage under various conditions, dsDNA samples in 10% AG or 10% pullulan (control polymer) were dried at 25° C. After drying, two types of long-term preservation experiments were performed: (1) storage at various temperatures and constant humidity and (2) storage at various humidity and constant temperature.

Figure 15A:
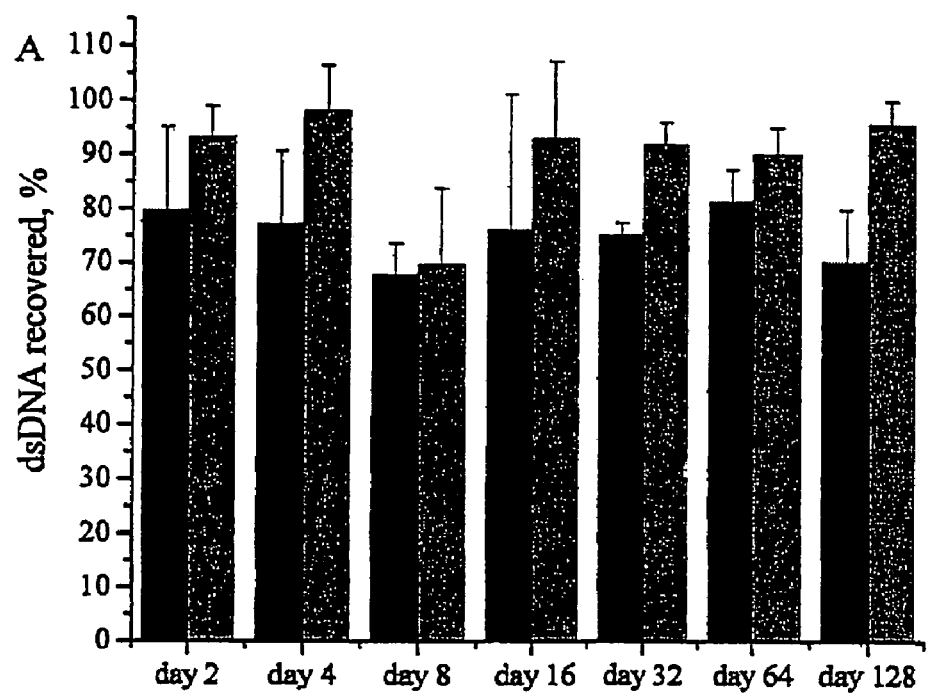
FIGS. 15A-15D are graphs illustrating the amounts of intact dsDNA recovered from AG (black bars) and pullulan (gray bars) that were stored at various temperatures in accordance with experiment 5 where samples were stored at 5° C.
Figure 15B:
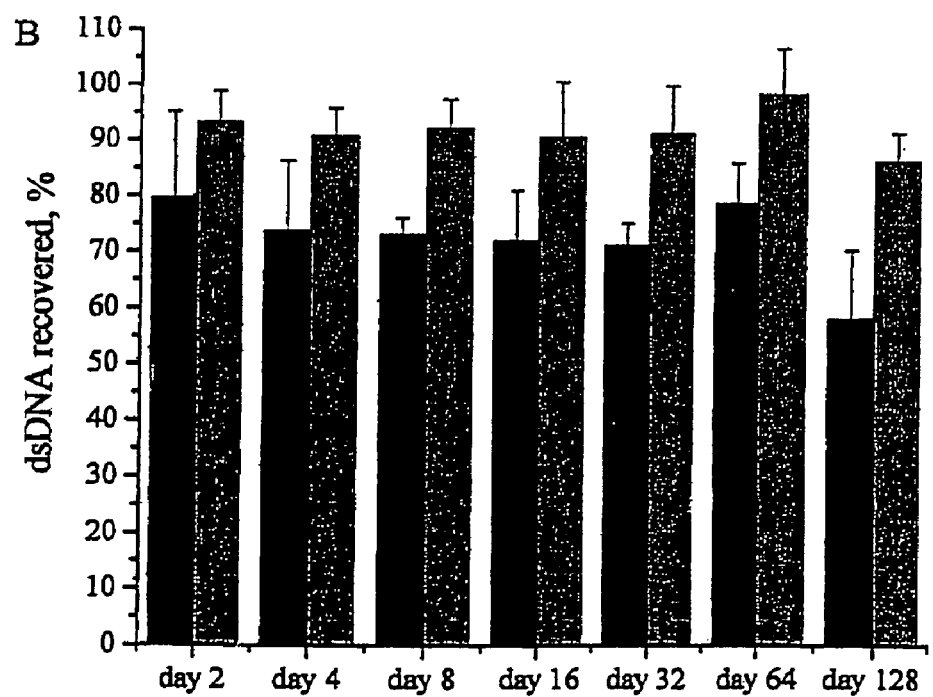
Figure 15C:
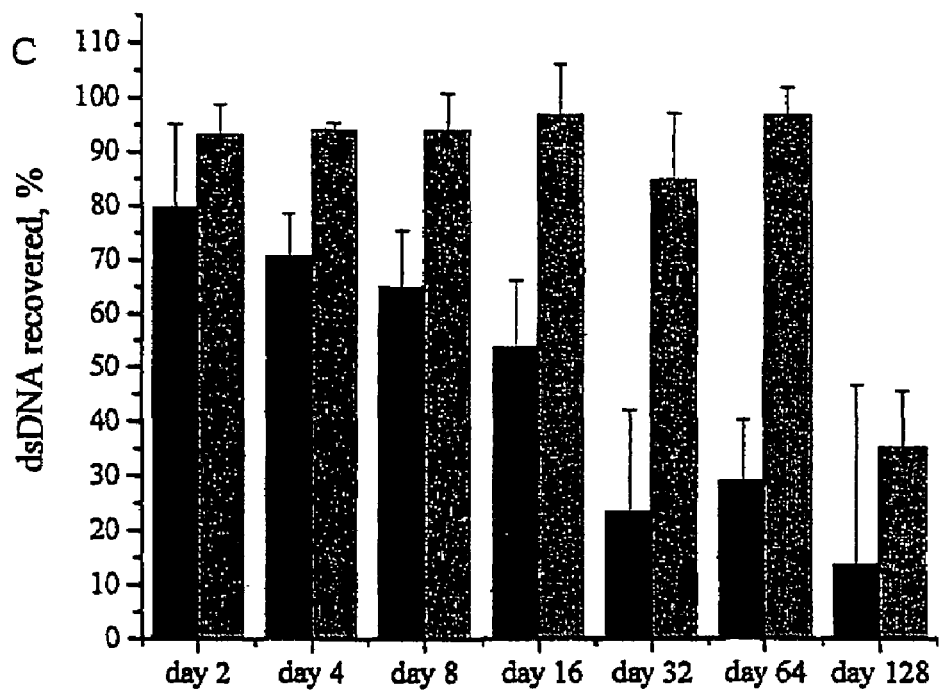
Figure 15D:
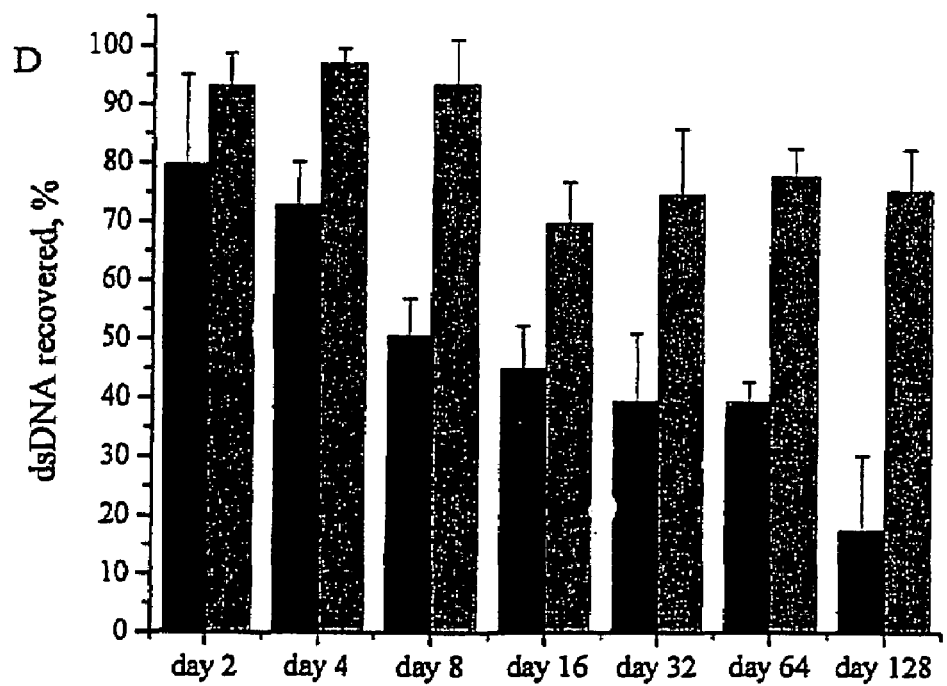

For dsDNA temperature experiments, samples were dried, stored at 5, 15, 25, or 40° C. and constant humidity (~33%) and dsDNA integrity was tested on days 2, 4, 8, 16, 32, 64 and 128 of storage. The relative amounts of intact dsDNA recovered from AG and pullulan samples after drying were 79.7 and 93.1%, respectively. The relative amounts of dsDNA recovered from AG stored at 5 and 15° C. tested on day 4 were 77.0 and 73.6%, respectively (FIGS. 15A-15B). After this initial period, there appeared to be no significant degradation of dsDNA up to day 64 for AG samples stored at 5 and 15° C. However, the relative amounts of dsDNA recovered from AG stored at 25 and 40° C. significantly declined on day 16 and day 8, respectively (FIGS. 15C-15D).

For pullulan samples, no significant degradation occurred after the drying process. The relative amounts of intact dsDNA from pullulan samples stored at 5, 15 and 25° C. up to day 64 were 90.0, 98.4 and 96.5%, respectively (FIGS. 15A-15D). These samples were comparable to control stored at −20° C. in TE buffer. Pullulan samples stored at 40° C. were remarkably consistent and similar to controls until day 16 with a slight decline to 69.7%, but less than that of AG samples (44.9%). It was evident that dsDNA were more stable in pullulan polymer through the drying and storing process than in AG polymer. Intact dsDNA were recovered from both formulations at all storage temperatures up to day 64.

Figure 16A:
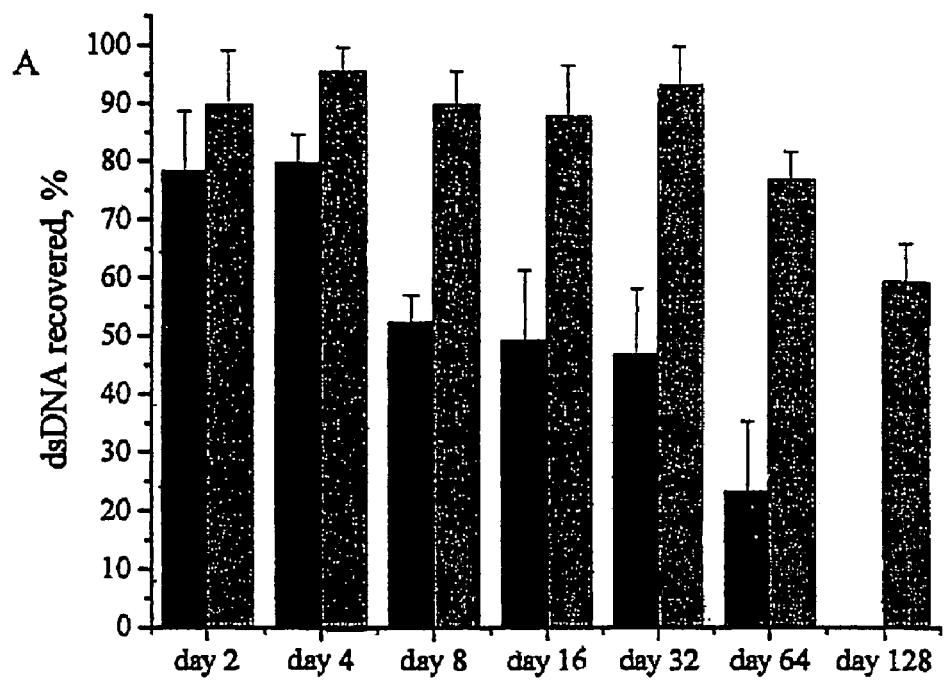
FIGS. 16A-16D are graphs illustrating amounts of intact dsDNA recovered from AG (black bars) and pullulan (gray bars) that were stored at various humidity in accordance with experiment 5 where samples were stored at 46% humidity (FIG. 14A), 53% humidity (FIG. 14B), 76% humidity (FIG. 14C) and 86% humidity (FIG. 14D).
Figure 16B:
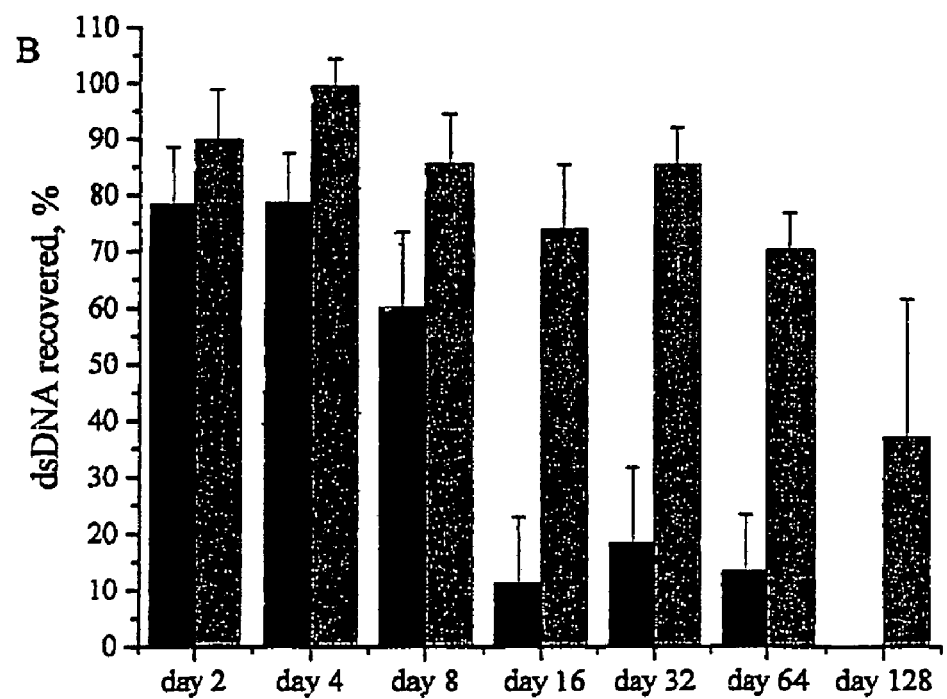
Figure 16C:
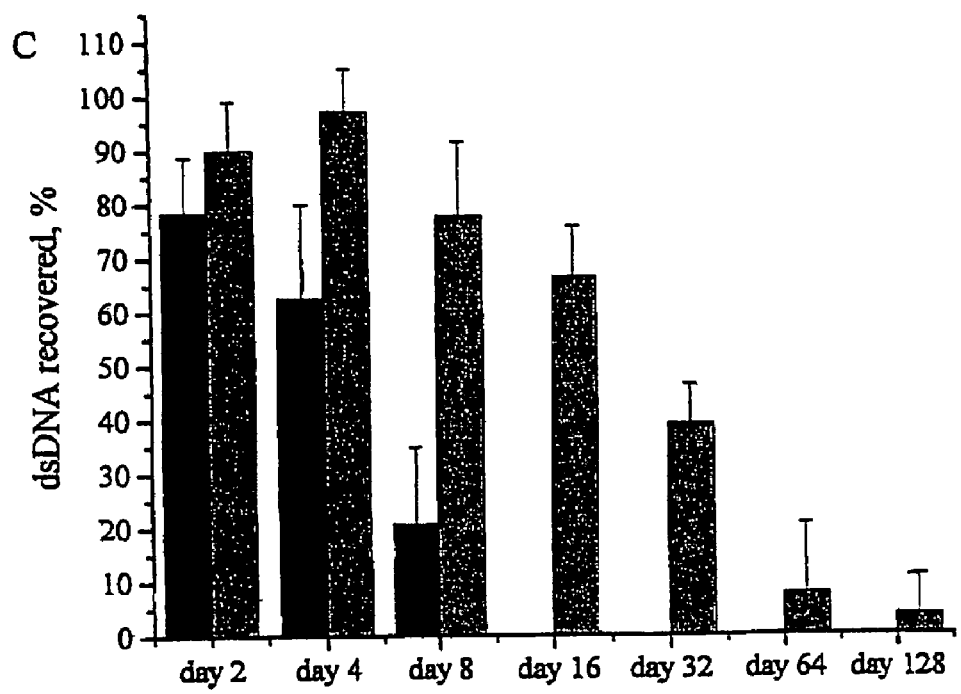
Figure 16D:
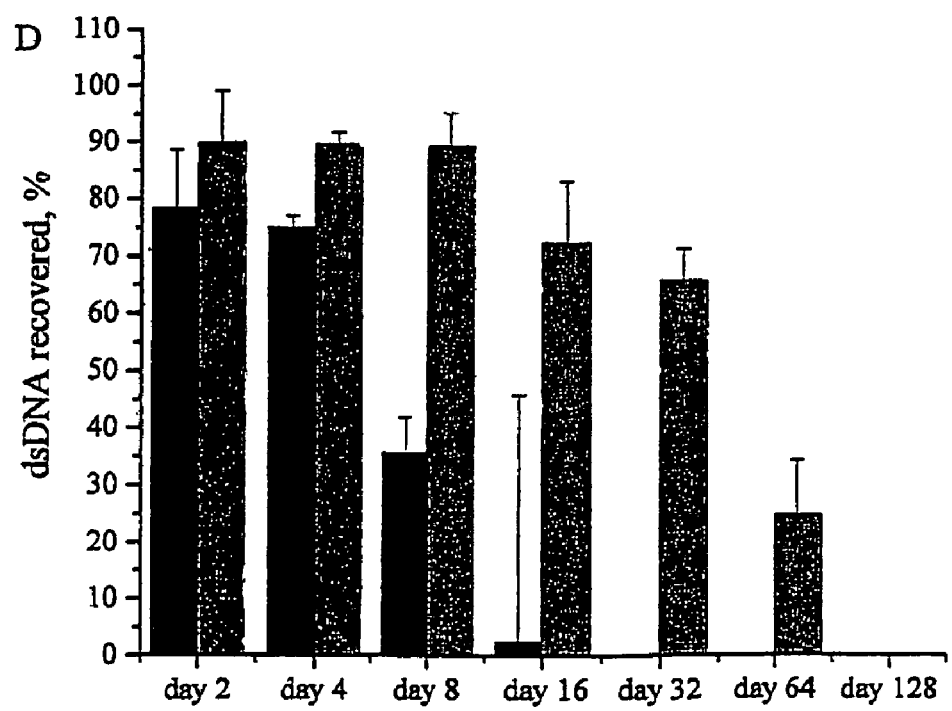

Similar to dsDNA temperature experiment, in the humidity experiment the samples were dried for two days and tested. The relative amounts of intact dsDNA for AG and pullulan samples after drying were 78.3 and 89.8%, respectively. The relative amount of dsDNA recovered from AG samples stored at 46 and 53% humidity began to decline on day 2 and became more noticeable on day 8 (FIGS. 16A-16B). Intact dsDNA were recovered from storage at 46 and 53% of humidity on day 64 but the amount was significantly less than control, 23.1 and 13.4%, respectively. The relative amounts of dsDNA recovered from AG samples stored at 76 and 86% humidity on day 8 were 20.6 and 35.5%, respectively (FIGS. 16C-16D). There was a small amount of detectable dsDNA on day 16 for AG samples stored at 86%, but no intact dsDNA were detected for samples stored at 76% humidity on day 16. On day 32, there was not detectable dsDNA for either AG samples stored at 76 or 86% humidity.

dsDNA samples preserved in pullulan were more stable than dsDNA in AG. Samples stored at 46 and 53% humidity were similar to dsDNA pullulan samples stored at 25° C. (FIGS. 16A-16B). dsDNA pullulan samples stored at higher humidity recovered much less intact dsDNA with time. On day 64, the relative amounts of dsDNA recovered for 76 and 86% humidity were 7.6 and 24.6%, respectively.

Discussion

The work described here was the first known study that utilizes *Acacia* gum (AG) and pullulan polymers as a protectant for desiccated ssDNA and dsDNA. ssDNA was unstable and degraded fast during drying for 2 days at room temperature in both polymers. Once dried, more intact ssDNA was recovered from AG samples than pullulan for all conditions tested. There was no detectable ssDNA in AG and pullulan samples stored at elevated temperatures. On day 118 of preservation, successful PCR amplification for both types of ssDNA samples was accomplished. The sequence obtained from control ssDNA which was stored in TE buffer at −20° C. was identical to experimental samples. dsDNA was very stable when preserved in both polymers and stored at cool temperatures up to 128 days. Degradation of dsDNA was faster for AG samples than pullulan samples when stored at elevated temperatures, and all humidity levels tested. Nonetheless, intact dsDNA preserved in AG was detected up to day 128 day for samples stored at 33% humidity and 25 and 40° C. and up to 64 days for samples at 46 and 53% humidity at 25° C.

The results obtained in these experiments show that AG and pullulan polymers protect DNA when dried and stored under various conditions using an inexpensive and simple process. DNA integrity could be prolonged when preserved in AG if mo e is known about the mechanism of DNA degradation during the drying process and storage in AG. For example, AG is a heterogeneous mixture of carbohydrates and proteins (Schmitt, Sanchez et al. 1998) and contains calcium, magnesium, potassium and sodium (Duke 1983). It is possible that the AG used in this study contained divalent cations. The presence of divalent cations ($Mg^{+2}$, $Ca^{2+}$ and $Ba^{2+}$ and $Mn^{2+}$) are well known to effect oligonucleotide conformations (Patil 2002), and binding of these cations to DNA has been shown to effect stability (Davey and Richmond 2002). Other factors that may contribute to a decrease in DNA integrity could involve the loss of water (Wu, Koch et al. 2005) and the low pH of AG. In addition, enzymatic processes, temperature, humidity, and oxidation contribute to DNA degradation. The most favorable conditions for preservation of DNA are reported to be low humidity and temperature and absence of microorganisms (Poinar and Stankiewicz 1999).

This method is applicable for transporting DNA samples because no refrigeration is needed for recovery of adequate amounts of DNA for the use in laboratory setting. In our study, the PCR products amplified from ssDNA samples preserved in protective polymers were sequenced using specific primers. The sequences of all samples tested were identical to control ssDNA stored in TE buffer at −20° C. Degradation of ssDNA in AG and pullulan samples is fast and no ssDNA is detected when samples are stored at elevated temperatures on day 128. PCR products of the correct size were obtained from ssDNA stored in AG and pullulan at different conditions for 118 days. When the amplified DNA were sequenced, there were no discrepancies between the DNA sequence of the experimental samples and control.

Conclusions ssDNA is sensitive to temperature degradation even in the presence of protective polymers, AG and pullulan. The greatest amount of intact ssDNA was recovered from AG samples when stored at 5 and 15° C. and low humidity (46 and 53%). In spite of fast degradation, PCR products of the correct size were obtained from ssDNA stored in AG and pullulan at different conditions for 118 days. These PCR products when sequenced were identical to control. dsDNA is resistant to degradation. For all storage conditions, intact dsDNA was recovered up to 64 days in pullulan. dsDNA was recovered from AG and pullulan up to 128 days when stored at cool temperatures. For all storage temperatures studied, more dsDNA was recovered from pullulan samples than AG.

Other Uses

The present invention offers a method of reversibly preserving biological specimens in a variety of contexts. The isolation and preservation techniques of the present invention could be used, without limitation, for isolating microbial cultures for shipment, blood isolation and storage, time-release capsules for pharmaceuticals, biodegradable packaging, soluble prostheses and implants, surgery, and forensics.

The polymer solution and the isolation and preservation techniques of the present invention represent a simple, rapid, and inexpensive alternative to many of the biological preservation techniques in use today. *Acacia* gum and pullulan are both organic, water-soluble, biocompatible, biodegradable, and non-toxic. The preservation of biological specimens with *Acacia* gum and/or pullulan is reversible and causes little or no damage to the specimen.

While this invention has been described in specific detail with reference to the disclosed embodiments, it will be understood that many variations and modifications may be effected without departing from the invention as described in the appended claims.

We claim:

1. A solid containing a reversibly preserved microorganism in a dormant and preserved state comprising:
   a cured suspension comprising the microorganism in an isolated condition combined with an effective amount of a pullulan solution, wherein said suspension is cured under ambient conditions to form a solid containing said microorganism in a dormant and preserved state;
   wherein the suspension can be restored by irrigating said solid under ambient conditions with an effective amount of an aqueous solution to restore said suspension and the suspension can be separated such that said microorganism is restored to said isolated condition.

2. The solid of claim 1, wherein the pullulan solution comprises a quantity of solid pullulan dissolved in a quantity of distilled water.

3. The solid of claim 1, wherein the microorganism is selected from a group consisting of bacteria, yeast, and fungi.

4. The solid of claim 1, wherein the microorganism is a bacterium.

5. A method of preparing the solid of claim 1, comprising:
   combining the microorganism in the isolated condition with the effective amount of the pullulan solution to form the suspension; and
   curing the suspension in ambient conditions to form the solid containing the microorganism in a dormant and preserved state.

6. The method of claim 5, wherein the pullulan solution comprises a quantity of solid pullulan dissolved in a quantity of distilled water.

7. The method of claim 5, wherein the step of curing further comprises stuffing the suspension.

8. The method of claim 5, wherein the step of combining comprises immersing the microorganism into an effective amount of a pullulan solution.

9. The method of claim 5, wherein the step of curing further comprises distributing the suspension over a surface to accelerate curing.

10. The method of claim 5, wherein the microorganism is a bacterium selected from the group consisting of *Escherichia coli*, *Salmonella* and *Bacillus subtilis*.

11. A method of restoring the reversibly preserved microorganism contained in the solid of claim 1, the method comprising:
    irrigating the solid in ambient conditions with an effective amount of an aqueous solution to restore the suspension; and
    separating the suspension such that the microorganism is substantially restored to the isolated condition.

12. The method of claim 11, wherein the aqueous solution comprises a quantity of distilled water, a buffer, a quantity of one or more compounds selected from the group consisting of potassium chloride, sodium chloride, magnesium chloride, and calcium chloride.

13. The method of claim 12, wherein the buffer comprises a quantity of 3-(N-morpholino) propanesulfonic acid.

14. The method of claim 11, wherein the microorganism is a bacterium selected from the group consisting of *Escherichia coli*, *Salmonella* and *Bacillus subtilis*.

* * * * *

UNITED STATES PATENT AND TRADEMARK OFFICE
CERTIFICATE OF CORRECTION

PATENT NO. : 7,604,807 B2
APPLICATION NO. : 11/341152
DATED : October 20, 2009
INVENTOR(S) : Vodyanoy et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 615 days.

Signed and Sealed this

Fourteenth Day of December, 2010

David J. Kappos
*Director of the United States Patent and Trademark Office*